US005846537A

United States Patent [19]

Rosebrough

[11] Patent Number: 5,846,537

[45] Date of Patent: Dec. 8, 1998

[54] MODIFIED AVIDIN AND STREPTAVIDIN AND METHODS OF USE THEREOF

[75] Inventor: Scott F. Rosebrough, Avon, N.Y.

[73] Assignee: University of Rochester, Rochester, N.Y.

[21] Appl. No.: 484,139

[22] Filed: Jun. 7, 1995

[51] Int. Cl.[6] ........................ A61K 39/395; A61K 39/44; C07K 17/00

[52] U.S. Cl. ........................ 424/178.1; 424/1.49; 424/9.1; 424/9.34; 424/9.35; 424/179.1; 424/183.1; 530/395; 530/402; 530/403; 530/406

[58] Field of Search .................................... 530/395, 402, 530/403, 406; 424/1.49, 9.1, 9.34, 9.35, 178.1, 179.1, 183.1

[56] References Cited

U.S. PATENT DOCUMENTS

| | | | |
|---|---|---|---|
| 4,401,647 | 8/1983 | Krohn et al. | 424/1.5 |
| 4,863,713 | 9/1989 | Goodwin et al. | 424/1.1 |
| 5,171,578 | 12/1992 | Bally et al. | 424/450 |
| 5,326,778 | 7/1994 | Rosebrough | 514/387 |

OTHER PUBLICATIONS

Marshall, et al. (1995) "Galactosylated Streptavidin for Improved Clearance of Biotinylated Intact and F $(ab')_2$ Fragments of an Anti–Tumour Antibody" *British Journal of Cancer 71*:18–24.

Marshall, et al. (1996) "Polyethylene Glycol Modification of a Galactosylated Streptavidin Clearing Agent: Effects on Immunogenicity and Clearance of a Biotinylated Anti–Tumour Antibody" *British Journal of Cancer 73* (5) :565–572.

Hiller et al. (1987) "Bioton binding to avidin" *Biochem. J. 248*:167–171.

Hnatowich et al. (1987) "Investigations of avidin and biotin for imaging applications" *J. Nucl. Med. 28*:1294–1302.

Kalofonos et al. (1990) "Imaging of tumor in patients with indium–111–labeled biotin and streptavidin–conjugated antibodies: preliminary communication" *J. Nucl. Med. 31*:1791–1796.

Kang et al. (1994) "Use of neutral avidin improves pharmocokinetics and brain delivery of biotin bound to an avidin–monoclonal antibody conjugate" *J. Pharmacol. Exp. Ther. 269*:344–350.

Mattes (1987) "Biodistribution of antibodies after intraperitoneal or intravenous injection and effect of carbohydrate modifications" *JNCI 79*:855–863.

Ong et al. (1991) "Galactose–conjugated antibodies in cancer therapy: properties and principles of action" *Cancer Research 51*:1619–1626.

Rosebrough (1993) "Plasma stability and pharmacokinetics of radiolabeled deferoxamine–biotin derivatives" *J. Pharmacol. Exp.Ther. 265*:408–415.

Rosebrough (1993) "Pharmacokinetics and biodistribution of radiolabeled avidin, streptavidin and biotin" *Nucl. Med. Biol. 20*:663–668.

Wilchek et al. (1993) "Avidin–biotin immobilisation systems" in *Application of Immobilized Molecules*, Sletyr et al., eds., Springer Verlag, NY, 51–60.

Winkelhake et al. (1976) "Aglycosylantibody" *J. Biol. Chem. 251*:1074.

*Primary Examiner*—Ponnathapura Achutamurthy
*Attorney, Agent, or Firm*—Scully, Scott, Murphy & Presser

[57] ABSTRACT

The present invention provides modified avidin and streptavidin compounds that have suitable blood clearance kinetics for use in a two-step approach to deliver a molecule to a target site. In particular, to hasten SA's blood clearance carbohydrate moieties are covalently bonded to SA. To prolong Avid's blood clearance, Avid is deglycosylated and/or neutralized by alkylation of its lysine amino acids. In a two-step approach, biotinylated compounds are used to deliver radionuclides, cytotoxic drugs, MRI agents, fluorochromes and other agents suitable for imaging and therapy to target-bound modified streptavidin or avidin conjugated antibodies or other targeting agents.

15 Claims, 17 Drawing Sheets

GC4-mal

SMCC

GC4-mal

GC4-SA Cross-linking

ATA-SA-X $\xrightarrow{NH_2OH}$ SH-SA-X + GC4-Mal $\longrightarrow$ GC4-SA-X

X = $NH_2$, NH-gal or NH-Tgal

MODIFIED AVIDIN AND STREPTAVIDIN AND METHODS OF USE THEREOF

FIELD OF THE INVENTION

The present invention provides modified avidin and streptavidin compounds that have optimal blood clearance kinetics for use in a two-step approach to deliver a molecule to a target site. In particular, to hasten streptavidin's blood clearance, carbohydrate moieties are covalently bonded to streptavidin. To prolong avidin's blood clearance, avidin is deglycosylated and/or neutralized by alkylation of its lysine amino acids. The present invention further provides targeting agents, such as monoclonal antibodies, conjugated to modified streptavidin and avidin. In a two-step method of imaging or therapy, biotin conjugates are used to deliver radionuclides, cytotoxic drugs, magnetic resonance imaging agents, fluorochromes and other agents suitable for imaging and therapy to target-bound conjugates of modified streptavidin or avidin and antibodies or other targeting agents.

BACKGROUND OF THE INVENTION

Various diagnostic, therapeutic, fluorescent and enzyme linked applications utilize cell or tissue specific targeting agents as delivery systems for radioactive, paramagnetic, cytotoxic or therapeutic agents. Any agent which is specific for a lesion or site of interest can potentially act as a targeting agent. For example, polyclonal and monoclonal antibodies can be produced which exhibit considerable specificity for certain cell or tissue types. Many other agents, including toxins such as diphtheria toxin, exhibit cell specificity and can be used to deliver diagnostic or therapeutic agents. The technique of delivery of monoclonal antibodies (MAbs) has been investigated for cancer therapy as well as for diagnosis of cancer, thromboembolism and cardiac myopathy.

For successful imaging with directly labeled antibodies, sufficient labeled MAb must localize at the target site to provide enough signal for detection. Target-to-background ratios must be high in order to achieve adequate contrast between target-bound radioactivity and background levels in other organs, tissues and blood. A major obstacle to successful imaging with directly labeled antibodies is the high background activity of free circulating radiolabeled MAbs due to prolonged circulation and accumulation in liver and spleen, the normal metabolic sites for Abs. Furthermore, the toxic effects of high radiation doses must be considered in both radioimmunotherapy and radioimmunoimaging. Such obstacles are also a consideration for methods utilizing targeting agents other than monoclonal antibodies.

Galactose protein modification has been utilized in an attempt to manipulate clearance of antibodies. For example, Ong et al. (1991) *Cancer Res.* 51:1619 and Mattes (1987) *JNCI* 79:855 have conjugated galactose to radiolabeled MAbs to manipulate the blood clearance rate of the MAbs in both diagnostic and therapeutic techniques. U.S. Pat. No. 4,401,647 discloses the galactose modification of albumin for liver imaging. Vera et al. (1985) *J. Nucl. Med.* 26:1157 and Stadalnik et al. (1992) *Investig. Radiol.* 28:64 have conjugated galactose to albumin for functional imaging studies of the liver. Both of these procedures result in radionuclide accumulation in the liver. This is problematic for imaging liver or chest lesions. In addition, liver metabolism increases, which creates problems for imaging and therapy due to accumulation of radioactivity in radiosensitive organs and tissues, especially bone marrow.

To overcome such obstacles, "pre-targeting" approaches have been investigated. See, e.g., Hnatowich, et al (1987) *J. Nucl. Med.* 28: 1294. In the conventional one-step method the radionuclide is linked to the MAb either directly or via a bifunctional chelating agent. In the pre-targeting approach the antibody is unlabeled, but conjugated to a binding moiety such as avidin or streptavidin. Unlabeled antibody is administered, and antibody which does not localize to the target site is allowed to clear from circulation or removed by a clearing agent before the administration of radioactivity. The radioactivity is then administered in a chemical form which has high affinity for the antibody, e.g., bound or chelated to the binding partner of the moiety conjugated to the antibody.

To provide the diagnostic or imaging agent in a form with high affinity for the antibody, two-step methods have been designed to exploit the high affinity of avidin and streptavidin for biotin. Avidin, a 67 kilodalton (kD) glycoprotein found in egg whites, has an exceptionally high binding affinity ($K_d$=$10^{-15}$M) for biotin. Avidin consists of four subunits, each capable of binding one biotin molecule. Streptavidin, a similar protein produced in *Streptomyces avidinii*, shares significant conformation and amino acid composition with avidin, as well as high affinity and stability for biotin. However, streptavidin is not glycosylated and reportedly exhibits less non-specific binding to tissues. Streptavidin is widely used in place of avidin because of its lower non-specific binding. Biotin, a member of the B-complex vitamins, is essential for amino acid and odd-chain fatty acid degradation, gluconeogenesis and fatty acid synthesis and is normally found in the enzyme bound form as biocytin.

In the prior art approach to radioimaging or radiotherapy, antibodies are coupled with either biotin or streptavidin and administered to the subject, followed by administration of radiolabeled streptavidin or biotin, respectively. Hnatowich et al. (1987); Kalofonos et al. (1990) *J. Nucl. Med.* 31:1791; Paganelli et al. (1992) *Eur. J. Nucl. Med.* 19:322; Yao et al (1995) *J. Nucl. Med.* 36:83. A three-step approach, which involves the administration of biotinylated antibody, followed by streptavidin and then radiolabeled biotin, has also been investigated. Paganelli et al. (1988) *Int. J. Cancer* 2:121. These multistep procedures generally require large doses of protein, and long time durations, often days, to complete. In particular, the prolonged circulation of streptavidin-conjugated antibodies requires either a significant time interval to allow clearing or the use of a clearing agent before administration of radiolabeled streptavidin or biotin. Paganelli et al. (1992) *Eur. J. Nucl. Med.* 19:322; U.S. Pat. No. 4,863,713 to Goodwin et al. Conversely, lavidin conjugated moieties would be expected to clear too quickly, and would likely not be useful in pre-targeting approaches due to unacceptably low target accumulation.

Accordingly, the pre-targeting method of the prior art is a complicated system that suffers from practical limitations, including, for example, the pharmacokinetics of avidin and streptavidin. Streptavidin and avidin exhibit markedly different pharmacokinetics after intravenous injection, with avidin clearing from the blood much faster than streptavidin. Thus, for a rapid two step procedure, streptavidin-containing moieties clear slowly, necessitating a delay in the injection of radiobiotin until blood levels have decreased. Conversely avidin clears too quickly and accumulates in the liver and kidney, thus resulting in low target accumulation. Avidin's rapid blood clearance results from its inherent positive charge and its mannose terminal sugars which may bind to mannose receptors present in the liver on Kupffer cells.

Thus, the directly labeled antibody approaches of the prior art suffer from background dosimetry problems, and the pretargeting approaches of the prior art are complicated, requiring large doses, multiple steps, and significant amounts of time to perform.

The present invention overcomes the deficiencies of the prior art. In particular, the present invention provides modified avidin and streptavidin compounds that have optimal blood clearance kinetics for use in a rapid method for delivery of an agent to a target site. Further, the avidin and streptavidin compounds of the invention are not radiolabeled, thus avoiding interference from background activity. Because of the optimal clearance kinetics of the present compounds, any of the subsequently administered radiolabeled biotin that does not become target bound is quickly filtered and removed from the body. The present invention thus satisfies the prior art need for a rapid and efficient method of imaging and therapy.

SUMMARY OF THE INVENTION

Figure 1:
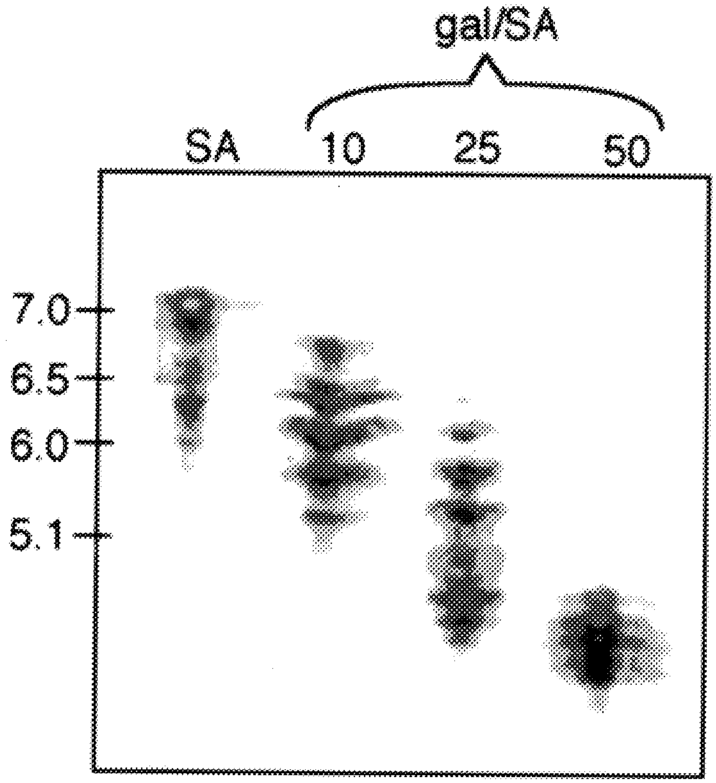
FIG. 1 represents isoelectric focusing of streptavidin (SA) and streptavidin-galactose (SA-gal) samples. The ordinate represents the isoelectric point and the abscissa represents molar incubation ratios of galactose.

The present invention provides modified avidin (Avid) and streptavidin (SA) compounds that have blood clearance kinetics suitable for use in diagnostic and therapeutic methods. In particular, to hasten streptavidin's blood clearance carbohydrate moieties are covalently bonded to streptavidin. To prolong avidin's blood clearance, avidin is deglycosylated and/or neutralized by alkylation of its lysine amino acids.

The present invention further provides conjugates of modified avid or SA and a targeting agent. In a preferred embodiment the targeting agent is an antibody or antibody fragment.

A further aspect of the present invention provides a method to deliver a diagnostic or therapeutic agent to a target site. The method of delivery of a diagnostic agent comprises administering to a host a modified Avid or SA conjugated to a targeting agent in an amount sufficient to bind to a target site, followed by administering a detectable biotinylated compound under conditions to form a complex with the Avid or SA conjugated targeting agent and at a dose sufficient for detection. The resulting complex is then detected. In a preferred embodiment the targeting agent is an antibody or antibody fragment. In a preferred embodiment, the present method utilizes fibrin specific MAbs for the diagnosis of intravascular lesions.

The method of delivery of a therapeutic agent comprises administering to a host a modified Avid or SA conjugated to a target agent, followed by administering a therapeutic biotinylated compound under conditions sufficient to form a complex with the Avid or SA conjugated targeting agent and at a therapeutically effective dose. In a preferred embodiment the targeting agent is an antibody or antibody fragment.

Yet another aspect of the present invention provides pharmaceutical compositions containing the subject conjugates and a pharmaceutically acceptable carrier. A compartmentalized kit for imaging or therapy is also provided by the present invention.

DETAILED DESCRIPTION OF THE INVENTION

The present invention provides modified avidin (Avid) and streptavidin (SA) compounds that have blood clearance kinetics suitable for use in a two step approach to deliver a molecule to a target site. The present compounds are useful in a method of delivering a diagnostic or therapeutic agent to a target site. In the present method, the modified Avid or SA is conjugated to a targeting agent and delivered to a host in an amount and under conditions to bind to a target site. A detectable or therapeutically effective biotinylated compound is then administered under conditions to form a complex with the modified Avid or SA conjugated targeting agent and at a dose sufficient for detection or therapeutic efficacy.

Modified Avid and SA compounds having suitable blood clearance kinetics for two step imaging or therapy are defined herein as compounds that, when conjugated to a targeting agent, circulate long enough to accumulate at a target site in sufficient amounts to bind a detectable or therapeutically effective amount of a biotinylated compound and further that are sufficiently cleared from circulation before the subsequent administration of biotin. Sufficient clearance of circulating modified Avid or SA conjugates is that amount of clearance that prevents clinically or diagnostically unacceptable levels of background due to binding of a subsequently administered biotinylated compound to the circulating modified Avid or SA conjugates to a biotinylated compound. A subsequently administered biotinylated compound is one that is administered within 24 hours of administration of the modified Avid or SA conjugate. In a preferred embodiment the biotinylated compound is administered within six hours, or more preferably within one hour, of the administration of the Avid or SA conjugate.

The modified SA compounds of the present invention are cleared more rapidly from the circulation than unmodified SA. In particular, the present invention provides SA covalently modified to contain at least one carbohydrate moiety. While not intended to limit the present invention, it is likely that enhanced clearance of the modified SA compounds results from binding to the liver as galactose receptors. Because the SA compounds are internalized by the galactose receptor, there is a reduced potential of immunogenicity.

The modified SA compounds are prepared by covalently attaching a carbohydrate moiety through at least one of SA's twenty amino groups. The resulting compound may contain linker molecules that facilitate the conjugation of carbohydrate to SA. From one to twenty of SA's amino groups (of which sixteen are lysine amino residues and four are terminal amino residues) may be modified by conjugation to carbohydrate. Further, more than one carbohydrate unit may be bonded per SA amino group, for example by providing branched compounds. Preferred carbohydrate moieties are galactose, mannose, fructose and lactose. Galactose is particularly preferred. In a most preferred embodiment, trigalactose moieties are covalently bonded to SA through SA's amino groups.

The modified SA compounds of the present invention contain at least one carbohydrate moiety. The carbohydrate moiety is preferably covalently bonded through an amino group of SA. The carbohydrate moiety is preferably galactose. The galactose moiety may consist of more than one galactose unit. Trigalactose is particularly contemplated. In a preferred embodiment, from about 1 to about 20 of SA's amino groups are covalently bonded to galactose.

The carbohydrate-modified SA compounds of the present invention can be prepared by synthetic methods know in the art. Either or both of SA and carbohydrate may be derivatized with a reactive group to facilitate covalent bonding. For example, galactose can be covalently attached to SA via a nucleophilic reaction of SA's amino groups with a reactive galactose-containing species such as α-D-galactopyranosyl-phenylisothiolcyanate.

In a general procedure, α-D-galactopyranosyl-phenylisothiocyanate is solubilized in methanol and added to SA solubilized in 0.05M sodium phosphate/0.15 NaCl buffer. α-D-galactopyranosyl-phenylisothiocyanate is added to SA in molar ratios of 10, 25 and 50. The preferred galactose/SA incubation ratio is about 25 to 50. A ratio of 50 results in near saturation of SA's amino groups while maintaining adequate binding affinity for biotin. The resulting solution is then incubated overnight at room temperature and the resulting SA-gal product separated, for example, by ultrafiltration.

The resulting SA-gal product contains galactose moieties covalently bound to SA. This product can then be analyzed to determine the amount of galactose bonded per SA molecule. For example, the average bound ratio of galactose to SA can be determined indirectly by quantifying galactose concentrations in the ultrafiltrate by an anthrone calorimetric assay, a method known to one of ordinary skill in the art and described by Roe (1955) *J. Biol. Chem.* 212:335.

Modified SA compounds in which more than one carbohydrate moiety is covalently bonded through each SA amino group can also be synthesized by methods known in the art. For example, cluster glycosides suitable for attachment to proteins are known in the art. Lee (1978) *Carbohydrate Research* 67:509 disclose a trigalactose derivative, (6-aminohexamido)tris(B-O galactosyloxymethyl) methane (Tgal) containing three galactose moieties at one end and a primary amine at the other. Trigalactose is particularly preferred for SA modification in accordance with the present invention since synthetic triglycosides exhibit higher binding affinity to the galactose receptor compared to the corresponding monoglycosides. Connolly et al (1982) *J. Biol. Chem.* 257:939.

The present invention provides additional trigalactose derivatives suitable for coupling to proteins. The trigalactose derivatives are stable and conveniently prepared. In one embodiment, a sulfhydryl group is incorporated into Tgal by reacting Tgal with S-acetylthioacetic acid (SATA) to provide Tgal-ATA. For example, a 3/1 molar ratio of SATA in dimethylsulfoxide is added to Tgal in 0.1M $PO_4$ at pH 8.0 and incubated overnight at room temperature under $N_2$. Tgal-ATA can then be purified, for example, by G-10 SEPHADEX size exclusion chromatography. Tgal-ATA has the formula:

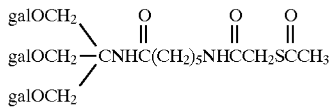

wherein gal is

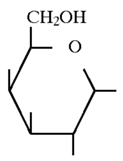

In another embodiment, a sulfhydryl group is incorporated into Tgal by reacting 2-iminothiolane (Traut's reagent) to provide Tgal-SH. For example, 2-iminothiolane is added in two equal aliquots to Tgal for a final molar ratio of 20/1 in 0.1M $PO_4$, 1 mM EDTA pH 7.6 and stirred for one hour at room temperature under $N_2$. Tgal-SH can then be purified, for example, by G-10 SEPHADEX size exclusion chromatography. Tgal-SH has the formula:

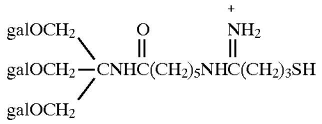

The trigalactose derivatives are utilized to covalently attach trigalactose moieties to SA through SA's amino groups by synthetic methods known in the art. For example, Tgal-ATA in 0.1M HOAc pH 4.0 is neutralized by the addition of solid $NaCO_3$ (final concentration 0.1M, pH 8.4) and a fifty fold molar excess is added to iodoacetylated SA. $NH_2OH$ is added to a final concentration of 0.05M and the solution mixed overnight at 37° C. under $N_2$. The resulting compound is SA covalently modified through SA's amino groups to contain trigalactose moieties (Tgal-SA). The synthesis of Tgal-SA is diagrammed in FIG. 14. Tgal-SA has the formula

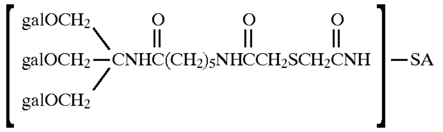

Wherein n is 1 to 20.

In another example, Tgal-SH in 0.1 M HOAc is neutralized by the addition of $NaCO_3$ (final concentration 0.1M, pH 8) and a fifty fold molar excess is added to iodoacetylated SA and the solution mixed overnight at 37° C. after purging with $N_2$. Excess Tgal is removed, for example by centrifugation using C30 CENTRICON filters and 0.05M $PO_4$, 0.15M NaCl pH 7.5 buffer. The resulting compound is SA covalently modified through its amino groups to contain trigalactose moieties.

The SA compounds containing covalently bonded carbohydrate moieties maintain the ability of SA to bind to biotin. For imaging or therapeutic methods in which a modified biotin or biotin derivative or analog is employed, the SA compounds of the invention may be derived from SA designed to bind to such a biotin species.

The ability of the SA compounds of the present invention to bind to biotin can be determined by assays known to one of ordinary skill in the art, for example by a biotin binding saturation assay as described hereinbelow.

For the trigalactose derivatives and modified SA compounds of the present invention, it is further contemplated to modify such compounds by alkylation of the carbohydrate moieties. In particular, alkylation and preferably acetylation of galactose moieties is contemplated. Alkylation can be accomplished by synthetic methods known to one of ordinary skill in the art, such as disclosed for example by Lee (1982) *Biochemistry* 21:1045; Lee (1982) *Biochemistry* 21:6292, and Stowell (1980) *Biochemistry* 19:4904. Alkylation of carbohydrate moieties prevents binding to the hepatic galactose receptor, and thus clearance of the subject compounds can be slowed, if desired, until the alkyl protecting group is removed by serum esterases. Tomic et al (1991) *Carbohydrate Res* 210:191. Acetylated trigalactose derivatives such as Tgal-ATA and Tgal-SH are particularly contemplated.

The Avid compounds of the present invention are provided by deglycosylating and/or neutralizing Avid. The modified Avid compounds have prolonged blood clearance relative to native Avid, and maintain the ability of Avid to bind to biotin. Deglycosylated Avid (Avid-E) can be provided by deglycosylating commercially available Avid by methods known in the art, for example, by enzymatic digestion with endoglycosidase-H. For example, 5 mg/ml Avid in 0.05M sodium citrate, pH 5.5, is digested with 0.1 unit per ml endoglycosidase-H (Sigma, St. Louis, Mo.) for 18 hours at 37° C. The extent of deglycosylation can be assessed by performing SDS-PAGE and observing a decrease in apparent molecular weight of Avid due to removal of oligosaccharide. Deglycosylated avidin may also be provided by recombinant methodology well-known to one of ordinary skill in the art.

Neutralized Avid (Avid-N) can be provided by alkylation of Avid's lysine residues by methods known in the art. Alkylation by lower alkyl groups (C1–C10) is preferred. Acetylation is most preferred. For example, Avid's lysine amino acids may be neutralized by incubation with an N-hydroxysuccinimide ester of acetate (NHS-Ac). More specifically, acetic acid N-hydroxysuccinimide ester is incubated with avidin at molar ratios of NHS-Ac/Avid ranging generally from 10 to 75. It is preferable that the molar ratio of NHS-Ac/Avid be below 50. Neutralization can be assessed by monitoring a progressive decrease in isoelectric point relative to native Avid, for example, by polyacrylamide isoelectric focusing.

In another aspect of the present embodiment, Avid is modified by both deglycosylation and neutralization of its lysine amino acids (Avid-E/N). A combination of deglycosylation and neutralization results in substantially longer clearance times. Avid-E/N is conveniently prepared by deglycosylating and then neutralizing Avid as described hereinabove.

The appropriate degree of deglycosylation and/or neutralization is that which results in prolonged blood clearance relative to native Avid while maintaining the ability of Avid to maintain to biotin, and further allows sufficient accumulation of a conjugated targeting agent at a target site in the absence of unacceptable background levels as defined above.

The modified Avid and SA compounds of the present invention maintain an adequate degree of the ability of native Avid and SA to bind to biotin. It is not necessary that the modified compounds exhibit the maximum tetrameric binding of Avid and SA for biotin. In a preferred embodiment, the present compounds exhibit at least about 25%, and more preferably about 50%, of the biotin saturation ratio of native Avid and SA as measured by an in vitro biotin binding saturation assay.

The ability of the compounds of the present invention to bind to biotin can be assessed by in vitro assays known to one of ordinary skill in the art. For example, the compounds of the present invention are incubated with a molar excess of radiolabeled biotin under conditions sufficient for avidin-biotin or streptavidin-biotin binding. Biotin bound to the tested compound is separated from unbound biotin, for example by filtration. The bound biotin/modified Avid or SA ratio is determined by dividing the activity in the retentate by the specific activity of the radiolabeled biotin. The binding ratios for each modified Avid or SA compound are determined by dividing the bound moles of biotin by the moles of each compound.

In a preferred embodiment, the radiolabeled biotin is the biotin chelate deferoxamineacetylcysteinylbiotin (DACB) labeled with $^{67}Ga$. DACB is known in the art and described for example by Rosebrough et al (1993) *J. Pharm. Exp. Therap.* 265:408 and in U.S. Pat. No. 5,326,778. DACB can be radiolabeled by direct addition of carrier free $^{67}Ga$ citrate (DuPont Merck Pharmaceutical Co., Billerica, Mass.). Samples of Avid, SA, modified Avid, and modified SA are incubated with a 20/1 molar excess of $^{67}Ga$-DACB on CENTRICON-30 filters (Amicon, Beverly, Mass.) in 0.05M Tris/0.15M NaCl, pH 7.5. After two washings, the bound DACB/protein ratio is determined by dividing the bound activity in the retentate by the specific activity of $^{67}Ga$-DACB. The binding ratio for each compound is determined by dividing the bound moles of DACB by the moles of each compound. Control Avid and SA generally exhibit a binding ratio of less than the maximum tetrameric binding of 4.0 in this assay. The modified Avid and SA compounds of the present invention exhibit binding ratios of at least about 25%, and more preferably greater than about 50%, of the binding ratio of control Avid and SA. The ordinarily skilled artisan can thus assess the compounds of the invention in the biotin binding assay to determine the appropriate amount of carbohydrate modification, deglycosylation and neutralization that is permissible without loss of biotin binding ability.

The blood clearance kinetics of the compounds of the present invention can be assessed by in vivo assays. The modified Avid and SA compounds are detectably labeled, for example by radiolabeling, injected into animals, and blood clearance is then determined by biodistribution analysis of radiolabeled samples. For example, the compounds of the present invention can be radiolabeled with $^{131}I$ by the Pierce lodobead method (Pierce, Rodeford, Ill.) and separated from free iodine for example by ultrafiltration using CENTRICON-30 filters. Experimental animals, for example, rabbits weighing about 3 kilograms, are fasted, anesthetized, and an external jugular vein is dissected and catheterized for injection and collection of blood samples. A radiolabeled compound of the present invention is injected. Whole blood samples are taken at various time intervals for about two hours. By comparing the blood clearance of galactose-modified SA with native SA, and Avid-E, the skilled artisan can determine the extent of modification that results in optimal blood clearance.

The present invention further provides targeting agents conjugated to modified SA and Avid. In a preferred embodiment the targeting agent bound to SA and Avid of the present invention is a protein or peptide. In a more preferred embodiment the targeting agent is a polyclonal or monoclonal antibody or fragment thereof. Antibodies contemplated by the present invention include anti-tumor antibodies, anti-fibrin antibodies, anti-myosin antibodies and any lesion-specific antibodies. Anti-fibrin and anti-myosin antibodies are particularly useful in cardiac imaging. Non-specific IgG is also useful in accordance with the present invention since it can be used in targeting of abscesses via Fc receptor binding. More preferred targeting agents include humanized or chimeric antibodies, human monoclonal or polyclonal antibodies, $F_v$ fragments, Fab fragments, $F(ab^1)2$ fragments, single chain antibodies (SCA), molecular recognition units (MRU) and synthetic genetically engineered binding proteins or peptides. The most preferred targeting agents are fibrin- or fibrinogen-specific MAbs for the diagnosis of intravascular lesions (e.g. thrombi, emboli and atherosclerosis). Antifibrin monoclonal antibody GC4 disclosed by Bini et al (1989) *Laboratory Investigation* 60:814 is particularly preferred. (ATCC No. ?).

Standard methods for the production and purification of antibodies and antibody fragments are known to one of ordinary skill in the art and can be found, for example, in *Antibodies: A Laboratory Manual*, Harlow et al., eds, (1988) Cold Spring Harbor Laboratory.

Methods for conjugating the modified avidin or streptavidin of the present invention to targeting agents are known to one of ordinary skill in the art. Either or both of the targeting agent and the modified Avid or SA may be derivatized with a reactive group to facilitate bonding. For example, Ishikawa (1980) *Immunoassay Supp.* 1:1 and Duncan et al (1982) *Anal. Biochem.* disclose methods of sulthydryl-maleimide coupling useful in the present invention. Kalofonos et al. (1990) *J. Nucl. Med.* 31:1791 and Hnatowich et al. (1987) *J. Nucl. Med.* 28:1294 disclose methods for conjugating an antibody with streptavidin and avidin, respectively, which use biotin as a linking group between the antibody and streptavidin or avidin. Other synthetic methods are well-known to one of ordinary skill in the art.

A preferred method to conjugate the modified SA or Avid of the invention to a monoclonal antibody comprises incorporating a sulfhydryl group into the modified Avid or SA and a reactive maleimide residue into the antibody, and reacting these species to form a conjugate in which the function of the antibody and modified Avid or SA are retained. A protected sulfhydryl group can be incorporated by S-acetylthioacetylation of modified Avid or SA with SATA. A reactive maleimide residue can be incorporated into an antibody for example by reaction of the antibody with succinimidyl 4-(N-maleimidomethyl) cyclohexane-1-carboxylate (SMCC). Alternatively, an antibody can be reacted with a variety of well-known bifunctional crosslinking agents that are reactive with a primary amine of the antibody and the sulfhydryl group of the modified Avid or SA.

Conjugates of modified SA and a targeting agent in which the carbohydrate residues of SA are protected by alkylation as described hereinabove are particularly contemplated.

The conjugates of modified Avid or SA and a monoclonal antibody or other targeting agent are capable of binding to biotin or a biotin derivative or analog, exhibiting clearance kinetics suitable to allow a timely subsequent administration of biotin, and binding to a target in amounts suitable for diagnosis or therapy. Biotin binding and clearance kinetics may be assessed as described hereinabove. The ability of the conjugate to bind to the target can be assessed by radiolabeling the conjugate, for example with $^{125}I$ or $^{131}I$ as described hereinabove, injecting the conjugate into experimental animals as described hereinabove, and taking planar gamma camera images at various time intervals for about two hours. At about two hours, animals are euthanized and major organs are removed and biodistribution of the radiolabeled conjugate is analyzed by counting organ samples in a gamma counter. By comparing the imaging profile of the unmodified targeting agent with the conjugated targeting agent, it can be determined that the conjugated targeting agent has maintained specificity for the desired target.

Another aspect of the present invention is directed to a method of delivering a diagnostic or therapeutic agent to a target site. The method of delivery of a diagnostic agent comprises administering a conjugate of a modified Avid or SA of the present invention and targeting agent to a host in an amount sufficient to bind to a target site, followed by administering a detectable biotinylated compound under conditions to form a complex with the target bound conjugate and at a dose sufficient for detection. The resulting complex is then detected. The method of delivering a therapeutic agent to a target site comprises administering a conjugate of a modified Avid or SA of the present invention and a targeting agent to a host in an amount sufficient to bind to a target site, followed by administering a biotinylated therapeutic agent under conditions to form a complex with the target-bound conjugate and at a therapeutically effective dose.

The conjugates of the present invention have optimal clearance kinetics for a method of diagnosis or therapy. The conjugates remain in the circulation long enough for sufficient localization to a target site, but non-target bound conjugates are cleared rapidly enough to avoid undesirable background. Accordingly, in the method of the present invention the biotinylated compound may be administered within 24 hours after administration of the conjugate. In a preferred embodiment, the biotinylated compound is administered within 6 hours, or more preferably within one hour, of administration of the conjugate.

A preferred embodiment of the present invention is a method of detection of a thrombus or embolus comprising administering a conjugate of a modified Avid or SA and a fibrin-specific monoclonal antibody, followed by administering a detectable biotinylated compound, and detecting the complex of the biotinylated compound and target-bound conjugate. In a preferred embodiment the biotinylated compound is radiolabeled DACB, and the SA is modified to contain trigalactose moieties.

The biotinylated compounds provide a delivery system for prodrugs, radioactive or paramagnetic metals, halogens, cytotoxins, chemotherapeutic drugs, fluorophores, enzymes or any other moiety that can be biotinylated.

Diverse classes of compounds, including proteins, polysaccharides, nucleic acids, haptens, peptides, chelating agents, halogenating agents, enzymes, fluorophores, lectins, cytotoxins, and drugs have been biotinylated in the prior art for a variety of applications. (See e.g. Diamondis et al. (1991) *Clin. Chem.* 37:625.)

Particularly preferred metal chelating agents include deferoxamine (DFO), diethylene-triaminopentaacetic acid (DTPA), ethylenediaminetetra-acetic acid (EDTA), bis-aminothiol (BAT, $N_2S_2$), ethylenediamine-di(O-hydroxphenylacetic acid) (EDHPA), 2,2-dipyridyl (DIPY), polyaminopolycarboxylate, tetrazacyclododecane tetracetate (DOTA), dithiocarbamate, dithiosemicarbazone (DTS), tetraazacyclotetradecane-tetracetate (TETA), hydroxamic acid derivatives and prophyrins. In a preferred embodiment the metal chelating agent is complexed with a metal. In a most preferred embodiment the metal is Tc-99m, $^{67}$Ga, $^{68}$Ga, $^{111}$In, $^{90}$Y, $^{186}$Re, $^{188}$Re, $^{212}$Bi, Fe, $^{52}$Fe or Gd.

Biotinylated compounds that contain a chelating agent are rendered detectable or therapeutically effective by labeling with a radioactive or paramagnetic metal. For radioimaging of a tissue or lesion of interest, it is preferred that the biotinylated compound is labeled with Fe, Gd, $^{52}$Fe, $^{68}$Ga, $^{99}$Tc, $^{111}$In, or $^{67}$Ga. For radioimmunotherapy, it is preferred that the DFO-biotin conjugate is labeled with $^{186}$Re, $^{188}$Re, $^{212}$Bi or $^{90}$Y. In radioimmunoimaging applications, administration of the labeled biotinylated compound is followed by detection of the complex. The method used for diagnostic imaging is appropriate for the particular metal in the compound. For example, paramagnetic metal ions such as Fe and Gd are suitable for nuclear magnetic resonance (NMR) analysis or magnetic resonance imaging (MRI). $^{52}$Fe and $^{68}$Ga are appropriate for analysis by positron emission tomography (PET), whereas $^{99m}$Tc, $^{111}$In and $^{67}$Ga can be detected by gamma camera imaging. The aforementioned means of image analysis are known to one of ordinary skill in the art and can be conducted in accordance with well-established techniques.

Similarly, the method of detection of other biotinylated compounds is dictated by the nature of the moiety that has been biotinylated. Detection is accomplished by methods known to one of ordinary skill in the art.

In another preferred embodiment, the biotinylated moiety contains a halogenating agent. Biotinylated compounds that contain a halogenating agent may be rendered detectable or therapeutically effective by labeling with a radioactive halogen. Preferred halogenating agents include tyramine, aniline, Bolton Hunter reagent and stannane. In an especially preferred embodiment the halogenating agent is radiohalogenated with an isotope of chlorine, bromine, iodine, fluorine or astatine. Preferred radioactive halogens include $^{211}$At, $^{77}$Br, $^{123}$I, $^{125}$I and $^{131}$I. Methods for detecting halogens are known to one of ordinary skill in the art.

In another preferred embodiment the moiety to be biotinylated is a fluorophore. Particularly preferred fluorophores are fluorescein, coumarin, rhodamine, phycoerythrin and Texas Red.

Preferred toxins include abrin, ricin, modeccin, Pseudomonas extoxin A, diphtheria toxin, pertussis toxin and Shiga toxin. Preferred enzymes include alkaline phosphatase, horseradish perioxidase, β-galactosidase and glucose oxidase. Preferred therapeutic drugs include methotrexate, vinblastine, doxorubicin, bleomycin, cisplatimun, urokinase and tissue plasminogen activator.

In the method of delivery of the present invention, compounds can be administered by well-known routes including oral, intravenous, intramuscular, intranasal, intradermal, subcutaneous, parenteral and the like. Dosage of the conjugates agents of the present invention and biotinylated compounds is an amount sufficient for the desired therapeutic or diagnostic effect, and can be determined by the ordinarily skilled artisan guided by appropriate dosages for similar methods of administration.

Another embodiment of the present invention provides a pharmaceutical composition comprising a conjugate of a modified Avid or SA and a targeting agent together with a pharmaceutically acceptable carrier. The compounds can be administered by well-known routes including oral, intravenous, intramuscular, intranasal, intradermal, subcutaneous, parenteral and the like. Depending on the route of administration, the pharmaceutical compositions may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

When the conjugates of the present invention are administered orally, the pharmaceutical composition thereof may also contain an inert diluent, an assimilable edible carrier and the like, be in hard or soft shell gelatin capsules, be compressed into tablets, or may be in an elixir, suspension, syrup or the like.

Preferred compositions of the conjugates provide diagnostically or therapeutically effective dosages. Effective dosages can be determined based upon the particular conjugate, the route of administration, size and health of the patient, and so on.

As used herein, a pharmaceutically acceptable carrier includes any and all solvents, dispersion media, coatings, antibacterial and antifungal agents, isotonic agents, and the like. The use of such media and agents are well-known in the art.

The present invention is also directed to a kit for delivery of a diagnostic or therapeutic agent. In one embodiment, the kit is compartmentalized to receive a first container adapted to contain a modified Avid or SA compound of the present invention conjugated to a targeting agent, and optionally a second container adapted to contain a biotinylated compound. In a preferred embodiment SA is modified to contain trigalactose moieties and the targeting agent is a monoclonal antibody. In an exemplified use of the subject kit, the contents of the first container are administered to a host. A metal chelating agent-containing biotinylated compound is labeled with a radioactive or paramagnetic metal and administered to the host within 24 hours after the administration of the targeting agent.

The following examples further illustrate the present invention.

EXAMPLE I

Synthesis and Characterization of SA-gal

This example provides the synthesis and characterization of modified streptavidin containing covalently bonded galactose moieties. Galactose was covalently bonded to SA via a nucleophilic reaction of the amino groups of SA with α-D-galactopyranosyl-phenylisothiocyanate.

SA (International Enzymes, Inc., Fallbrook, Calif.) was solubilized in 0.05 sodium phosphate/0.15 NaCl buffer, Ph 8.0 at a concentration of 10 mg/ml as determined spectrophotometrically at 280nm ($E_{1,280nm}{}^{1\%}$=34.0). α-Dgalactopyranosyl-phenylisothiocyanate (Sigma, St. Louis, Mo.) was solubilized in methanol and added to SA in molar incubation ratios of 10, 25 and 50 for overnight incubation at room temperature. The SA-galactose samples were then centrifuged using MICROCON-30 filters (Amicon, Beverly, Mass.).

Isoelectric focusing was performed to assess the conjugation of galactose to SA, since each conjugated galactose results in a decrease of one positive charge. Polyacrylamide isoelectric focusing (IEF) was performed using a BioRad mini IEF cell (BioRad Labs, Hercules, Calif.) with ampholytes ranging from Ph 3–8. A progressive decrease in the isoelectric point of SA-gal samples was observed with increasing molar ratios of galactose/SA, as shown in FIG. 1.

The molar ratio of bound galactose per SA was quantified by analyzing the ultrafiltrate by an anthrone calorimetric assay as reported by Roe [(1955) *J.Biol. Chem.* 212, 335–343]. For incubation ratios of 10, 25 and 50 the average bound ratios were 5, 8 and 19 respectively. SA contains 20 amino groups of which 16 are lysine amino and 4 are terminal amino residues. Thus, a galactose/SA molar ratio of 50 results in near saturation of SA with an average bound ratio of 19.

EXAMPLE II

Synthesis and Characterization of Avid-N, Avid-E and Avid-E/N

This example provides the synthesis of biochemically modified avidin, i.e. avidin neutralized by acetylation of its lysine amino acids (Avid-N), avidin deglycosylated by endoglycosidase-H (Avid-E), and avidin both neutralized and deglycosylated (Avid-E/N).

Avid (Sigma, St. Louis, Mo.) was neutralized by incubating acetic acid N-hydroxysuccinimide ester (NHS-Ac) (Sigma, St Louis, Mo.) with 5 mg/ml Avid in 0.05M sodium phosphate/0.15 NaCl buffer, Ph 8.0, at molar ratios of 10, 25, 50 and 75 for one hour at room temperature to produce Avid-N.

Avid or Avid-N at a concentration of 5 mg/ml in 0.05 M sodium citrate, pH 5.5 buffer was digested with 0.1 unit per ml endoglycosidase-H (Sigma, St. Louis, Mo.) for 18 hours at 37° C. to produce Avid-E or Avid-E/N, respectively.

Figure 2A:
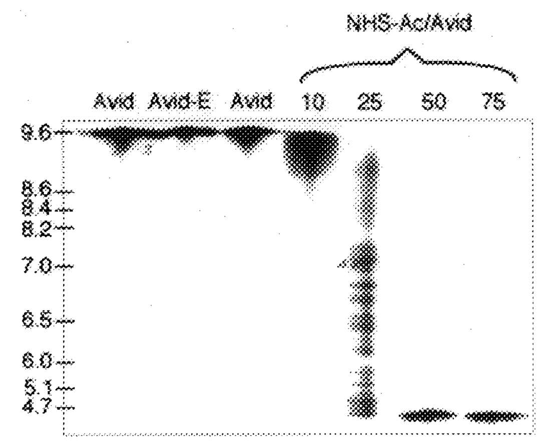
FIG. 2A represents isoelectric focusing of Avid and Avid-N.
Figure 2B:
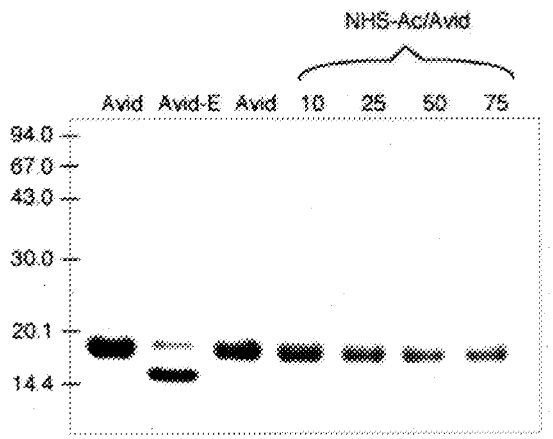
FIG. 2B represents sodium dodecyl sulfate polyacrylamide gel electrophoresis (SDS-PAGE) of Avid and Avid-N.

Avid-N and Avid-E were characterized by SDS-PAGE and IEF. SDS-PAGE was performed using a Bio-Rad mini-Proteam II cell (BioRad Labs, Hercules, Calif.) with 17% polyacrylamide gels. The results in FIG. 2B show that the subunits of Avid and Avid-N had equivalent molecular weights. Avid-E exhibited a decrease in molecular weight due to the removal of oligosaccharide. Polyacrylamide IEF was performed using a BioRad mini IEF cell (BioRad Labs, Hercules, Calif.) with ampholytes ranging from pH 3–10. As shown in FIG. 2A, neutralization resulted in a progressive decrease in isoelectric point, corresponding to the incubation ratio of NHS-Ac/Avid. Deglycosylation had no effect on the IEF of Avid.

EXAMPLE III

Synthesis of Tqal-SA

Figure 3:
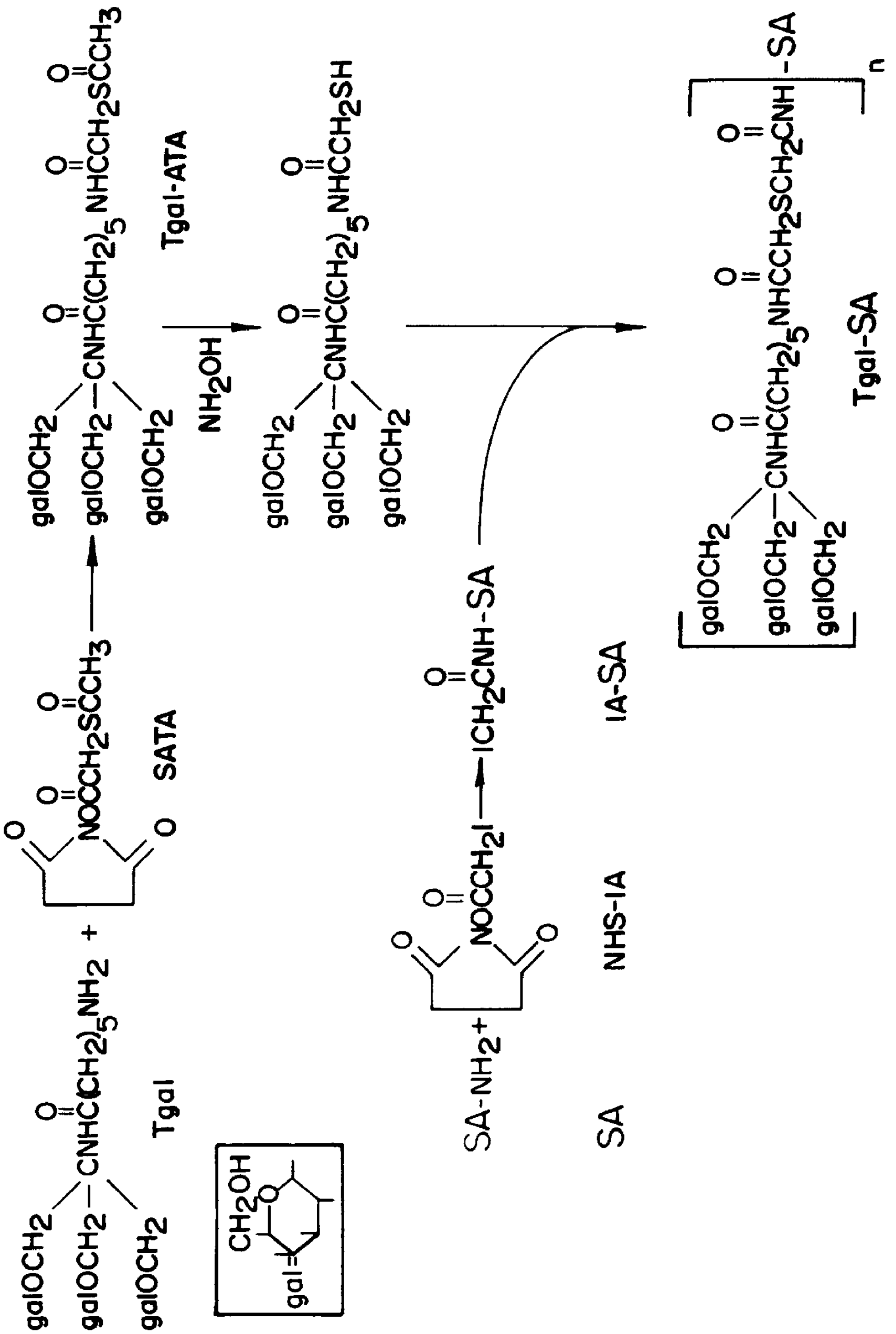
FIG. 3 diagrams the synthesis of Tgal-SA.

The trigalactose derivative (6-aminohexamido)tris(B-D-galactosyloxymethyl)methane (T-gal) has been synthesized and characterized by Lee (1978) *Carbohydrate Research* 67:509. Tgal contains three galactose moieties at one end and a primary amine at the other end. The trigalactose derivative of SA (Tgal-SA) was synthesized as follows and as outlined in FIG. 3.

Synthesis of Tetra-O-acetyl-α-D-galactosyl bromide (Compound 1)

Acetic anhydride (100 ml) and 70% perchloric acid (0.6 ml) were mixed at 5° C. and the solution was warmed to room temperature. D-galactose (10.0 grams, 27.54 mmol) was added to the stirred mixture over five hours at a rate that maintained the reaction temperature between 30°–40° C. The reaction mixture was stirred further for 30 minutes at 35° C. Red phosphorous (3.0 grams, 96.9 mmol) was added and the flask cooled in ice. Bromine (6.44 ml, 103.0 mmol) was added slowly to keep the reaction temperature below 20° C., and 15.0 ml of water added at 20° C. over a 30 minute period. The reaction mixture was stirred overnight at room temperature. Chloroform was added and the mixture filtered. The filtrate was washed with cold water three times and finally the organic layer was washed with a saturated solution of sodium hydrogen carbonate. The reaction mixture was dried over silicic acid, and chloroform was evaporated under reduced pressure. The product was crystallized in ether (50ml) and hexane (100 ml) yielding 6.0 grams of product, melting point 76°–77° C. (literature melting point 79°–84° C.). $^1$H NMR was in agreement with the structure of the compound.

Preparation of 6-(trifluoroacetamido)hexanoic acid (Compound 2)

6-Aminohexanoic acid (100 mmol, 13.1 g) was placed in a flask. Trifluoroacetic anhydride (270 mmol, 40.0 mL) was added to the flask at cold tap water temperature. After the addition of all trifluoroacetic anhydride, the reaction was brought to room temperature and stirred for one hour. The reaction mixture was evaporated at reduced pressure, 100 ml of cold water was added and the mixture stirred overnight at 5° C. The crystalline product was filtered off, washed with cold water, dried and recrystallized from ether yielding 8.0 grams of product, melting point 90°–91° C. (literature melting point 88°–89° C.). $^1$H NMR matched the structure of the compound.

Preparation of 2-(hydroxymethyl)-2-[6(trifluoroacetamido) hexanamide]-1,3-propanediol (Compound 3)

A mixture of 2-amino-2-(hydroxymethyl)-1,3-propanediol (20 mmol, 2.42 g), Compound 2 (25 mmol, 5.7g) and 2-ethoxy-N-(ethoxycarbonyl)-1,2-dihydroquinoline (30 mmol, 7.4 g) were boiled under reflux for 6 hours. The mixture was cooled to room temperature and evaporated to a syrup. Addition of ether yielded crystals. Recrystallization from ethyl acetate gave 4 grams of product with melting point of 100°–101° C. (literature melting point 97°–99° C.). $^1$H NMR was in close agreement with the structure of the compound.

Preparation of (6-aminohexamido)tris (β-D-galactosyloxymethyl)methane (Compound 4)

A mixture of Compound 1 (7.29 mmol, 3.0 g), Compound 3 (1.45 mmol, 0.48 g) and mercuric cyanide (7.3 mmol, 1.84 g) in 50 ml toluene:nitromethane (1:1, v/v) was stirred at 60° C. for 2 hours. Reaction mixture was evaporated and was extracted with chloroform. The organic layer was washed twice with 1M sodium chloride, dried and evaporated to a syrup. Silica gel TLC showed a single spot and therefore the compound was not purified further. The galactose assay gave a weight:galactose ratio of 1:3.

The resulting acetylated galactose compound was deprotected by stirring the syrup overnight with 20 mM barium methoxide (25 ml) and evaporating the reaction mixture under reduced pressure. The reaction mixture was treated with 1M sodium hydroxide (10 ml) and was stirred for 4 hours at room temperature. The pH of the reaction mixture was lowered to 3.0 by the addition of glacial acetic acid and was lyophilized. A portion (100 mg) of this mixture was dissolved in water and was purified by a column (2×100 cm) of SEPHADEX G-10 in 0.1M acetic acid. The elution was monitored at 220 nm and the first peak was collected and lyophilized (5 mg). The galactose assay of the product gave a weight:galactose ratio of 1:3. Electrospray mass spectral analysis showed a quasimolecular ion at m/z 721 $(M+H)^+$.

Preparation of SA-IA (Compound 5)

N-Hydroxysuccinimide iodoacetate (NHSIA, 1.17 mg) and SA (5 mg) were mixed in 50 mM phosphate buffer-saline containing 1 mM EDTA (pH 8.0). The reaction mixture was incubated for 1 hour at 37° C. and was washed with 50 mM phosphate buffer-saline on a Centricon-30 filter.

Preparation of Tgal-ATA (Compound 6)

A 3/1 molar ratio of SATA in DMSO was added to 30$\mu$moles of Tgal in 0.1M $PO_4$, pH 8.0, and incubated overnight at room temperature under $N_2$. Tgal-ATA was purified by G-10 SEPHEDEX size exclusion chromatography.

Preparation of SA-Tqal (Compound 7)

Tgal-ATA (Compound 6, 2.96 mg) and IA-SA (Compound 5, 2.0 mg) were incubated overnight in the presence of N-hydroxylamine (0.5M) in 50 mM phosphate buffer-saline containing 1 mM EDTA (pH 8.4) at 37° C. The bound Tgal-ATA:SA ratio was determined indirectly by the difference in galactose concentration in the incubation mixture and that of the first CENTRICON-30 filtrate a measured by the anthrone assay.

EXAMPLE IV

Biotin Binding Assay

This example demonstrates the ability of the modified avidin and streptavidin compounds of Examples I–III to bind to biotin.

The biotin chelate deferoxamine acetyl cysteinylbiotin (DACB) was prepared and purified as described by Rosebrough (1993) *J. Pharm. Exp. Therap.* 265:408 and U.S. Pat. No. 5,326,778.

Figure 4A:
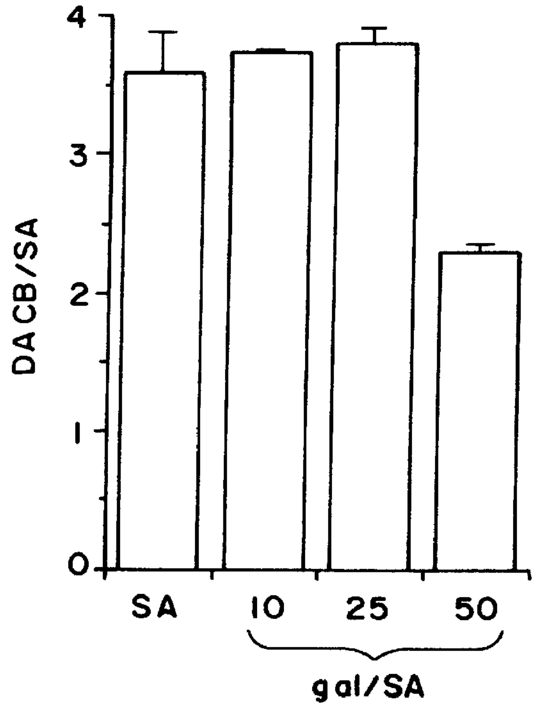
FIGS. 4A and 4B represent a deferoxamineacetyl cysteinyl biotin (DACB) saturation assay on SA, SA-gal, avidin (Avid) and neutralized avidin (Avid-N). The abscissa indicates molar incubation ratios of galactose or acetic acid N-hydroxysuccinimide ester (NHS-Ac) with protein. The ordinate indicates bound DACB/protein ratios.
Figure 4B:
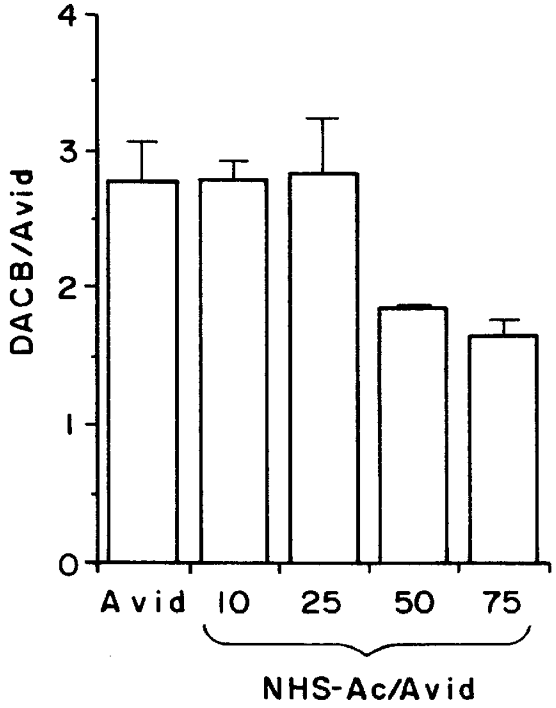

The purified DACB was then used to assess the ability of the compounds prepared in accordance with Examples I–III to bind to biotin. DACB was radiolabeled by direct addition of carrier free $^{67}$Ga citrate (Du Pont Merck Pharmaceutical Co., Billerica, Mass.). Separate samples of SA and Avid and modified SA and Avid prepared in accordance with Examples I–III, were incubated with a 20/1 molar excess of $^{67}$Ga DACB on CENTRICON-30 filters (Amicon, Beverly, Mass.) in 0.05 Tris/0.15M NaCl buffer, pH 7.5. After 2 washings, the bound DACB/protein ratio was determined by dividing the bound activity in the retentate by the specific activity of $^{67}$Ga DACB (~2x10$^{16}$cpm/mole). The binding ratios for each sample were determined by dividing the bound moles of DACB by the moles of each protein. As shown in FIG. 4A, control SA exhibited a binding ratio of 3.6, approximating maximum tetrameric binding. SA-gal samples with galactose/SA molar ratios of 10 and 25 exhibited no reduction in binding. The DACB saturation ratio for the SA-gal sample with a galactose/SA molar ratio of 50 was 2.3. As shown in FIG. 4B, DACB saturation analysis of Avid-N samples at molar ratios of 10 and 25 approximated the binding of DACB to native avidin. Like the modified SA compounds, the modified Avid compound did not exhibit a decrease in biotin binding until large amounts of lysine neutralization had occurred.

Similarly, Tgal-SA prepared in Example IV exhibited binding to DACB to the same extent as native SA.

EXAMPLE V

Biodistribution of Modified SA and Avid

SA (International Enzymes, Inc., Fallbrook, Calif.), Avid (Sigma, St. Louis, Mo.), SA-gal having average bound ratios of 5, 8 and 19 galactose moieties per SA (SA-gal-5, SA-gal-8, and SA-gal-19, respectively), SA-Tgal, Avid-E, Avid-N (50 NHS-Ac/1 Avid) and Avid-E/N prepared in accordance with Examples I–III were radiolabeled with $^{131}$I by the Pierce Iodobead method (Pierce, Rockford, Ill.) and free iodine removed by ultrafiltration using CENTRICON-30 filters. SA and Avid, 0.5 mg, were radiolabeled with starting activities of ~0.3mCi $^{131}$I and ~0.1mCi $^{131}$I, respectively. The radiolabeling yields were ~75% for SA and ~25% for Avid samples. When analyzed by Centricon-30 ultrafiltration, less than 5% free iodine was present in the injected samples.

Biodistribution was determined in vivo. New Zealand White rabbits, ~3 kg, (n=3 per experiment) were fasted for 12 hours prior to the experiment and anesthetized using an intramuscular injection of chlorpromazine (25 mg/kg) followed by intravenous sodium pentobarbital (15 mg/kg). An external jugular vein was dissected and catheterized using a 5 French straight catheter for injection and collection of whole blood. The animal was placed in a supine position under the gamma camera for imaging and was then injected with [75 $\mu$g] of the radiolabeled proteins prepared above. Whole blood samples (2–3 ml) were taken at intervals for 2 hours. Planar gamma camera images (30K count acquisition) were taken at 5, 30, 60 and 120 minutes. At two hours, animals were euthanized. Major organs were removed, weighed and representative samples taken for biodistribution analysis. Blood volume was estimated to be 6% of total body weight.

Figure 5B:
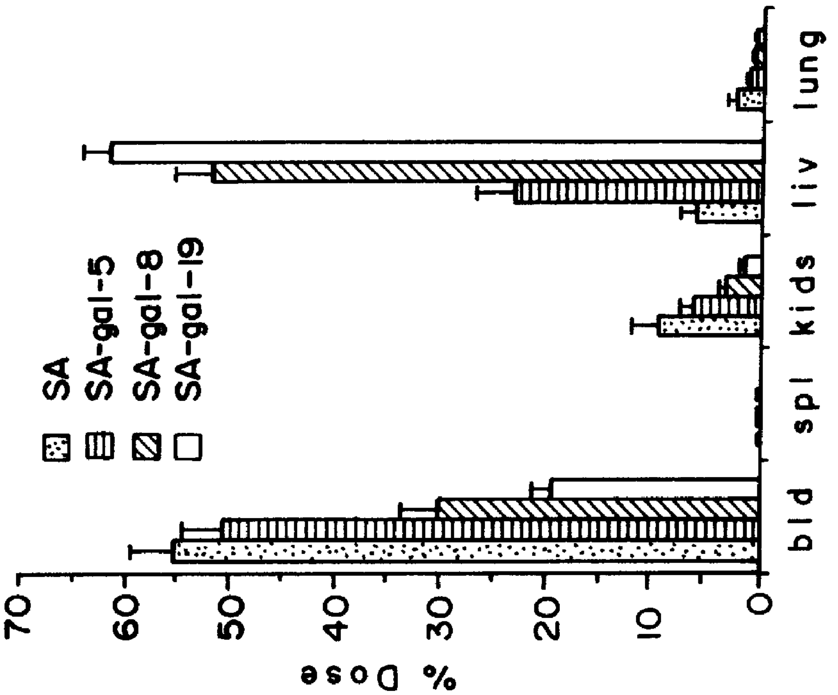
FIG. 5B represents the biodistribution of $^{131}$I-SA and $^{131}$I-SA-gal at 2 hours after injection in the blood, spleen, kidneys, liver and lung.
Figure 5A:
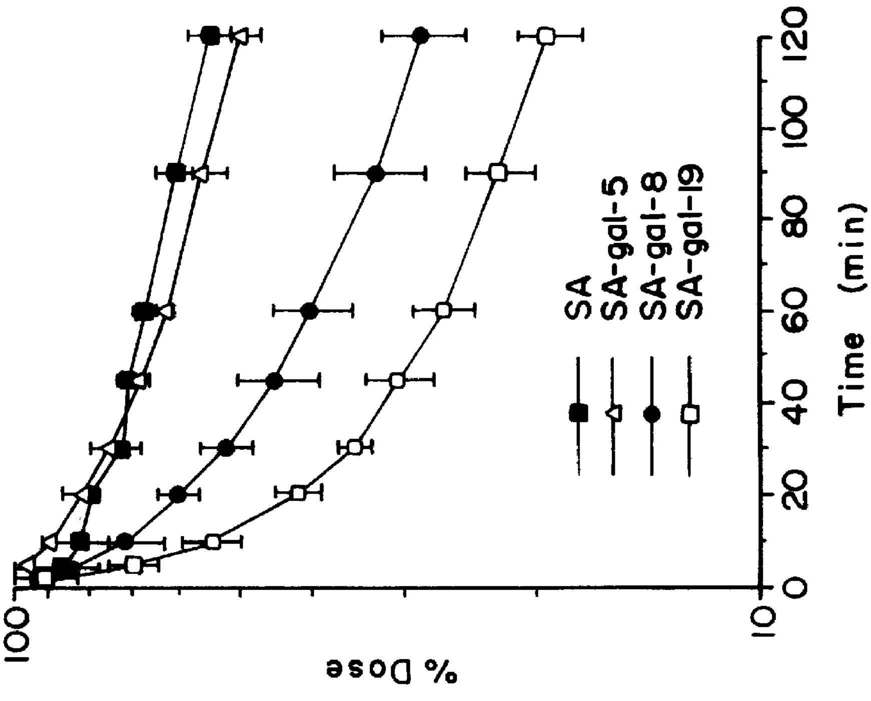
FIG. 5A is a graph showing blood pharmacokinetics of SA and SA-gal in rabbits. The abscissa represents time and the ordinate represents percentages of the injected dose of compound.
Figure 6:
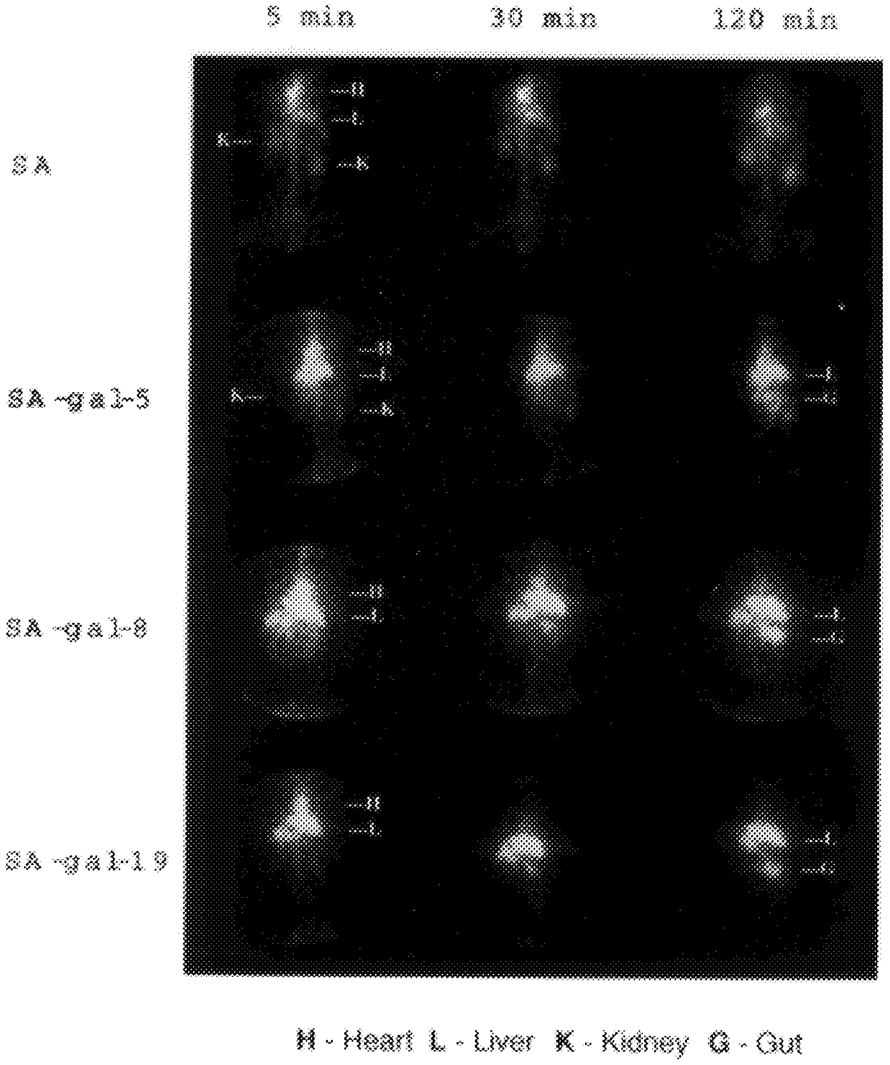
FIG. 6 represents nuclear images of $^{131}$I-SA and $^{131}$I-SA-gal at 5, 30 and 120 minutes after injection.
Figure 9:
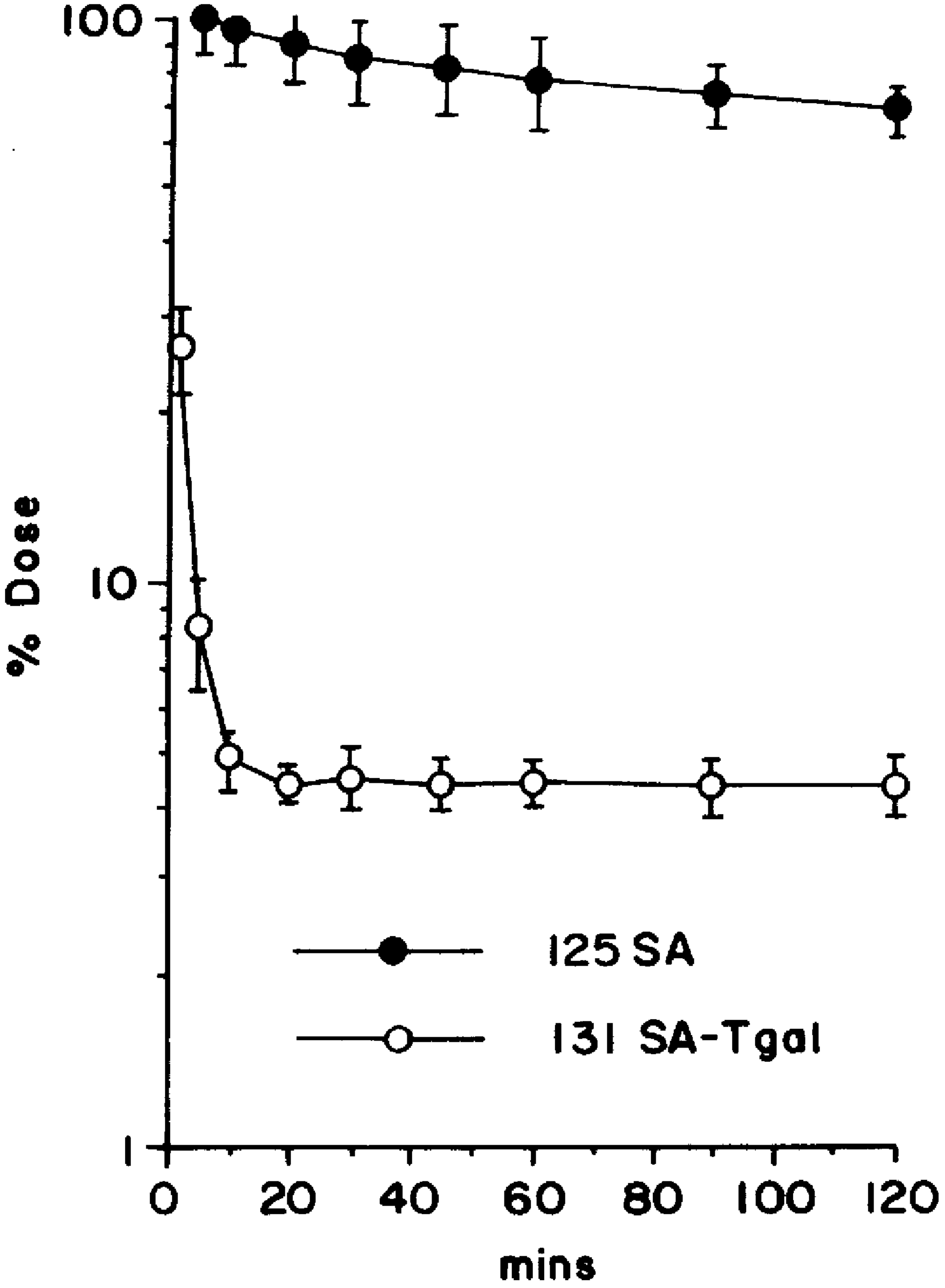
FIG. 9 is a graph showing blood pharmacokinetics of $^{125}$I-SA and $^{131}$I-streptavidin-trigalactose (SA-Tgal) in rabbits. The abscissa represents time and the ordinate represents percentages of the injected dose of compound.

FIG. 5A shows the blood clearance of samples of SA, SA-gal-5, SA-gal-8 and SA-gal-19. SA and SA-gal-5 circulated similarly with greater than 50% in the blood at 2 hrs. SA-gal-8 exhibited faster blood clearance with ~30% circulating at 2 hours, and SA-gal-19 exhibited the fastest clearance with 20% circulating at 2 hours. SA-Tgal, FIG. 9, shows the fastest clearance with approximately 4% circulating at 2 hours. Biodistribution results, FIG. 5B, indicate increasing hepatic uptake in correlation with the amount of galactose bound per SA. This is consistent with galactose receptor uptake by hepatocytes. Visual results from gamma camera images of rabbits injected with these samples were in agreement with the biodistribution results. $^{131}$I-SA images, FIG. 6, show vascular activity as indicated by systemic circulation and cardiac activity. $^{131}$I-SA-gal samples showed increasing hepatic uptake and decreased circulation with larger amounts of bound galactose. Hepatic metabolism, as evident by biliary and gut activity, was also present with $^{131}$I-SA-gal samples in the 30 and 120 minute images.

Figure 7B:
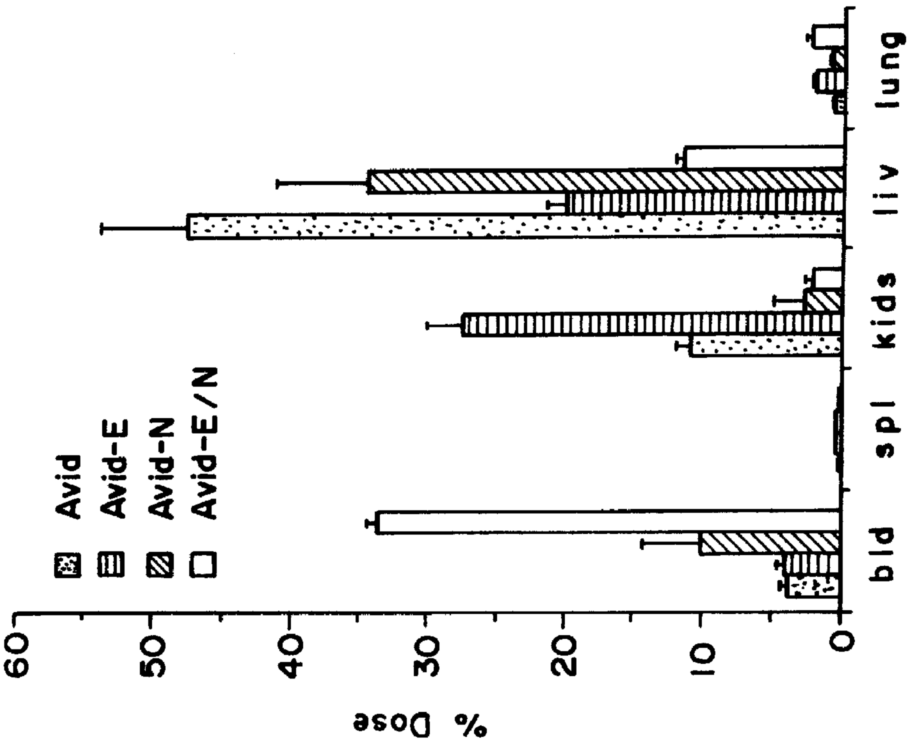
FIG. 7B represents the biodistribution of $^{131}$I-Avid, $^{131}$I-Avid-E, $^{131}$I-Avid-N and $^{131}$I-Avid-E/N at 2 hours after injection in the blood, spleen, kidneys, liver and lung.
Figure 7A:
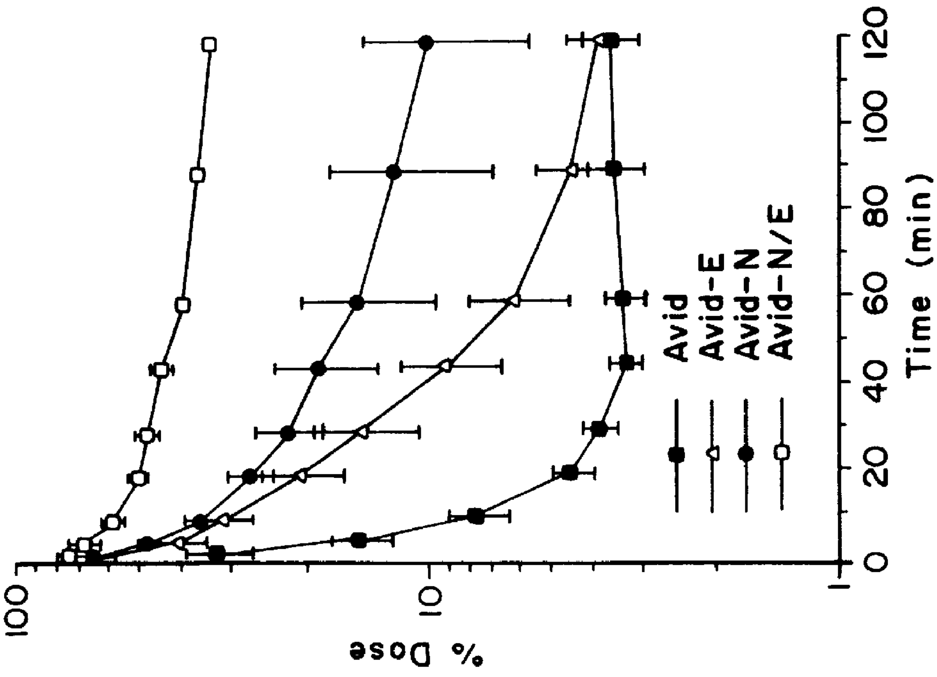
FIG. 7A is a graph showing blood pharmacokinetics of $^{131}$I-Avid, $^{131}$I-deglycosylated avidin (Avid-E), $^{131}$I-Avid-N, $^{131}$I-deglycosylated and neutralized avidin (Avid-E/N) in rabbits.

FIG. 7A shows the blood clearance of Avid, Avid-E, Avid-N and Avid-E/N. $^{131}$I-Avid cleared quickly from the circulation (FIG. 7A). $^{131}$I-Avid-E and $^{131}$I-Avid-N cleared slower than native Avid, and the blood clearance of $^{131}$I-Avid E/N was substantially prolonged with circulatory values at 2 hours approaching that of $^{131}$I-SA. Thus, each modification of Avid increased circulation time, with the slowest clearance resulting from a combination of deglycosylation and neutralization. Biodistribution results differed with each type of modification (FIG. 7B). $^{13}$I-Avid accumulated mostly in the liver and kidney. $^{131}$I-Avid-E kidney accumulation increased with a corresponding decrease in liver activity. Conversely, $^{131}$I-Avid-N kidney accumulation decreased considerably but had a high liver accumulation. With $^{131}$I-Avid-E/N, there were low levels in both the kidney and liver. These results suggest that the clearance of Avid consists of two mechanisms, one due to net charge and one resulting from specific sugar receptor binding.

Figure 8:
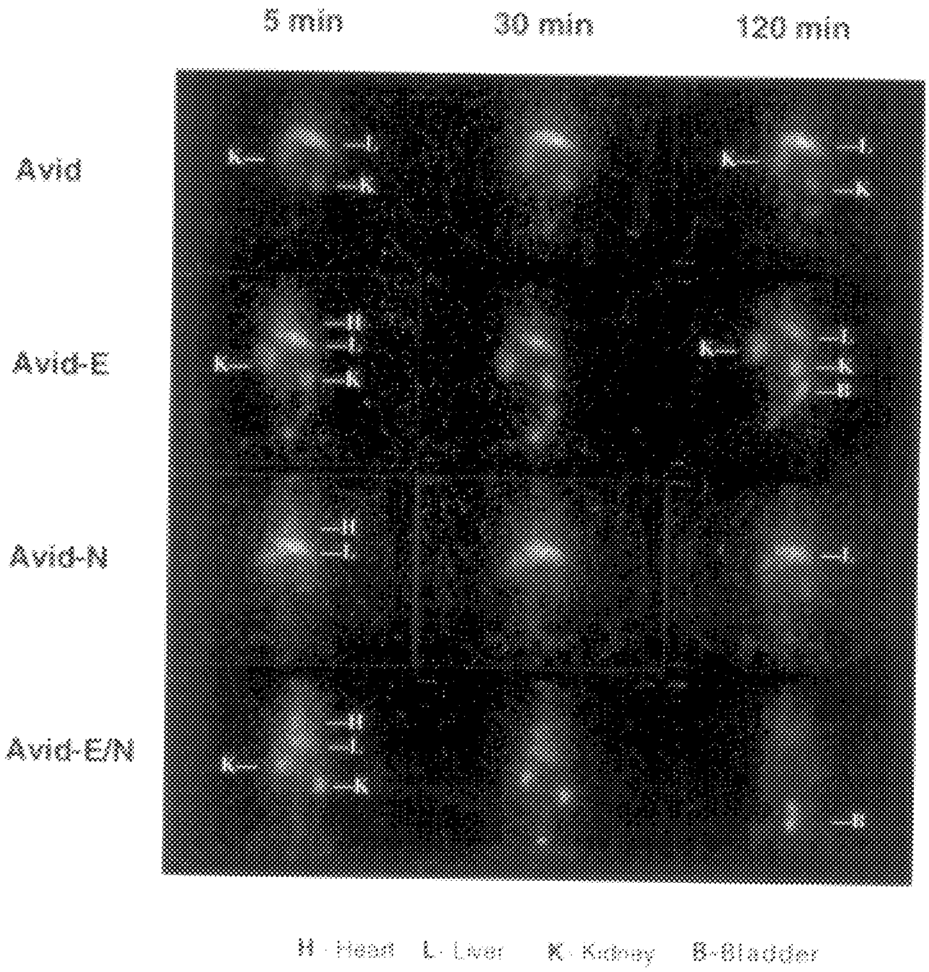
FIG. 8 represents nuclear images of $^{131}$I-Avid, $^{131}$I-Avid-E, $^{131}$I-Avid-N and $^{131}$I-Avid-E/N at 5, 30 and 120 minutes after injection.

FIG. 8 shows planar gamma camera images of $^{131}$I-Avid, $^{131}$I-Avid-E, $^{3}$I-Avid-N and $^{131}$I-Avid-E/N samples. Consistent with the biodistribution results, $^{131}$I-Avid activity was exclusively in the liver and kidneys. $^{131}$-Avid-E had increased kidney activity. $^{131}$I-Avid-N images showed a dramatic reduction in kidney activity and a corresponding increase in liver activity. $^{131}$I-Avid-E/N showed circulatory activity with a corresponding decrease in liver and kidney activity. Urine activity was present with $^{131}$I-Avid-E and $^{131}$I-Avid-E/N and when analyzed by C-30 centricon ultrafiltration, greater than 90% of the activity was protein bound.

Figure 10:
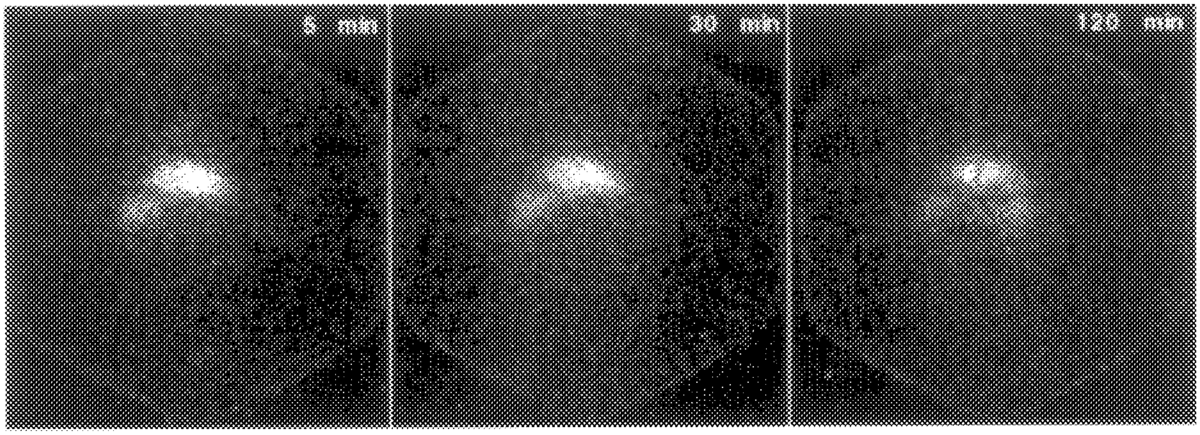
FIG. 10 is a composite of the nuclear images of $^{131}$I-gal-SA at 5, 30 and 120 minutes.

FIG. 10 shows planar gamma camera images of $^{131}$I-Tgal-SA at 5, 30 and 120 minutes. Consistent with the biodistribution results, $^{131}$Tgal-SA images demonstrated the liver as the single focus of tracer uptake with hepatic metabolism evident as indicated by gut activity in the 120 minute image.

EXAMPLE VI

Synthesis of SA-GC4, gal-SA-GC4 and Tqal-SA-GC4

Figure 11A:
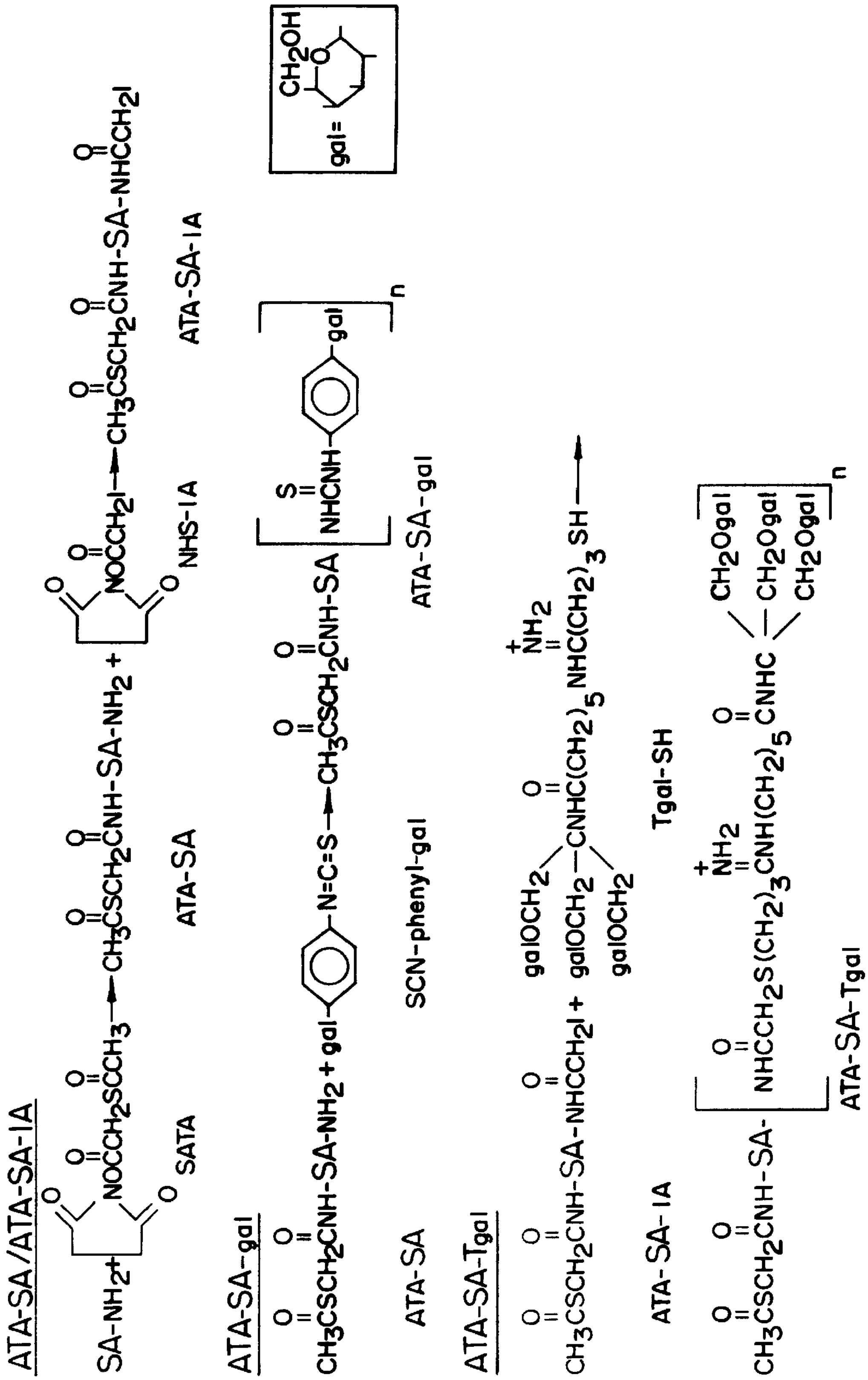
FIG. 11 is an outline of the synthesis of GC4-SA, GC4-SA-gal and GC4-A-Tgal.
Figure 11B:
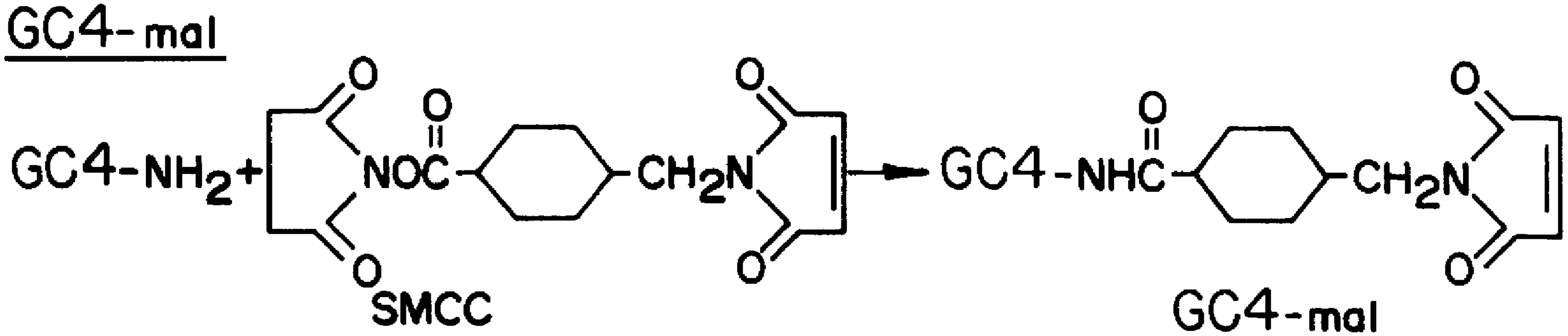

SA, SA-gal-19 and SA-Tgal were conjugated to GC4, an anti-fibrin monoclonal antibody by the addition reaction of sulfhydryl-containing SA derivatives with maleimide-GC4 (GC4-mal) (as diagrammed in FIG. 11).

Preparation of GC4-mal (Compound 8)

A five fold molar excess of succinimidyl 4-(N-maleimidomethyl)cyclohexane-1-carboxylate (SMCC) (Pierce, Rockford, Ill.) solubilized in DMSO was added to a 16.9 mg/ml solution of GC4 monoclonal antibody (Bini et al, 1989*, Arteriosclerosis* 9:109) in 0.05 $PO_4$/0.15M NaCl pH 7.5 buffer containing 1 mM EDTA for 1 hour. Excess SMCC was removed by centrifugation using C 30 CENTRICON filters and 0.05 $PO_4$/0.15M NaCl pH 7.5 buffer containing 1 mM EDTA.

Preparation of Tgal-SH (Compound 9)

2-Iminothiolane (Traut's reagent) was added in two equal aliquots (t=0 and 30 minutes) to Tgal, prepared according to Example III, for a final molar ratio of 20/1 in 0.1M $PO_4$/1mM EDTA pH 7.6 and stirred for one hour at room temperature under $N_2$. The resulting Tgal-SH was purified by G-10 SEPHADEX (2.0×100 cm) size exclusion chromatography 0.1M acetic acid running buffer at a flow rate of 1.5ml/min.

Preparation of ATA-SA-gal (Compound 10)

SA-ATA was prepared by adding a six-fold molar excess of SATA to a 5 mg/ml solution of SA in 0.05M $PO_4$/0.15M NaCl pH 6.5 buffer containing lmM EDTA for two hours at room temperature. Excess SATA was removed by centrifugation using CENTRICON-30 filters and 0.05M $PO_4$/0.15M NaCl pH 7.5 buffer containing 1mM EDTA.

A fifty-fold excess of α-D-galactopyranosylphenyl isothiocyanate (Sigma) solubilized in methanol was added to a 12 mg/ml solution of SA-ATA in 0.05 $PO_4$/0.5M NaCl pH 8 buffer overnight at room temperature. Excess galactose was removed by centrifugation using C 30 CENTRICON filters and 0.05 $PO_4$/0.5M NaCl pH 7.5 buffer containing 1 mM EDTA.

Preparation of Tgal-SA-ATA (Compound 11)

IA-SA-ATA was synthesized by adding a 50 fold excess of N-hydroxysuccinimide iodoacetamide (NHS-IA) in DMSO to a 5 mg/ml SA-ATA solution 0.05 $PO_4$/0.5M NaCl pH 8 buffer containing 1 mM EDTA and stirred overnight at 37° C. Excess NHS-IA was removed by centrifugation using C 30 CENTRICON filters and 0.05 $PO_4$/0.5M NaCl pH 7.5 buffer, containing 1 mM EDTA. A 50 fold excess of Tgal-SH (Compound 9) in 0.1M HoAC neutralized by the addition of $NaCO_3$ (final M=0.1M, pH=8), was added to IA-SA-ATA (final IA-SA-ATA concentration of 0.45 mg/ml) overnight at 37° C. after purging with $N_2$. Excess Tgal was removed by centrifugation using C 30 CENTRICON filters and 0.05 $PO_4$/0.5M NaCl pH 8 buffer.

Preparation of gal-SA-GC4 (Compound 12)

Equal molar, 0.65 $\mu$M, gal-SA-ATA (Compound 10) and GC4-mal (Compound 8) were mixed in 0.05 $PO_4$/0.15M NaCl pH 7.5 buffer containing 1 mM EDTA and 0.05M $NH_2OH$ overnight at room temperature. The gal-SA-GC4 conjugate was purified from unreacted GC4, SA-gal and GC4-GC4 aggregates by size exclusion chromatography (SUPEROSE 12, Pharmacia, Piscataway, N.J.). For SUPEROSE 12 chromatography, the running buffer was 0.05 $PO_4$/0.15M NaCl pH 9.0 at 0.3ml/min. For iminobiotin affinity chromatography, the second peak collected from the SUPEROSE 12 column was loaded with a 10 ml superloop onto a iminobiotin column. After the absorbance ($A_{280mn}$) returned to baseline, the GC4-SA conjugates were eluted by changing buffers to 0.1M sodium acetate pH 3.5. The eluent was then concentrated and the buffer exchanged by Centricon-30 centrifugation with 0.05 $PO_4$/0.15M NaCl pH 7.5 buffer. Each eluted protein peak was analyzed by SDS-polyacrylamide electrophoresis (to determine the extent of crosslinking) using a Bio Rad mini-Protean II cell (Bio Rad Labs, Hercules, Calif.) and 8.5% polyacrylamide gels.

Preparation of Tqal-SA-GC4 (Compound 13)

Equal molar, 0.65 $\mu$M, Tgal-SA-ATA (Compound 11) and GC4-mal (Compound 8) were mixed in 0.05 $PO_4$/0.15M NaCl pH 7.5 buffer containing 1 mM EDTA and 0.05 M $NH_2OH$ overnight at room temperature. The Tgal-SA-GC4 conjugate was purified from unreacted GC4, SA-Tgal and GC4-GC4 aggregates by size exclusion chromatography (SUPEROSE 12, Pharmacia, Piscataway, N.J.). For SUPEROSE 12 chromatography, the running buffer was 0.05 $PO_4$/

0.15M NaCl pH 9.0 at 0.3 ml/min. For iminobiotin affinity chromatography, the second peak collected from the SUPEROSE 12 (highly crossed-linked beaded agarose Suspension in 20% ethanol; Fractionation range: (MW) globular protein 1,000–300,000; wet bead diameter: 20–40 uM) column was loaded with a 10 ml superloop onto a iminobiotin column. After the absorbance ($A_{280mn}$) returned to baseline, the GC4-SA conjugates were eluted by changing buffers to 0.1M sodium acetate pH 3.5. The eluent was then concentrated and the buffer exchanged by CENTRICON-30 centrifugation with 0.05 $PO_4$/0.15M NaCl pH 7.5 buffer. Each eluted protein peak was analyzed by SDS-polyacrylamide electrophoresis (to determine the extent of crosslinking) using a Bio Rad mini-Protean II cell (Bio Rad Labs, Hercules, Calif.) and 8.5% polyacrylamide gels.

Preparation of SA-GC4 (Compound 14)

Figure 12:
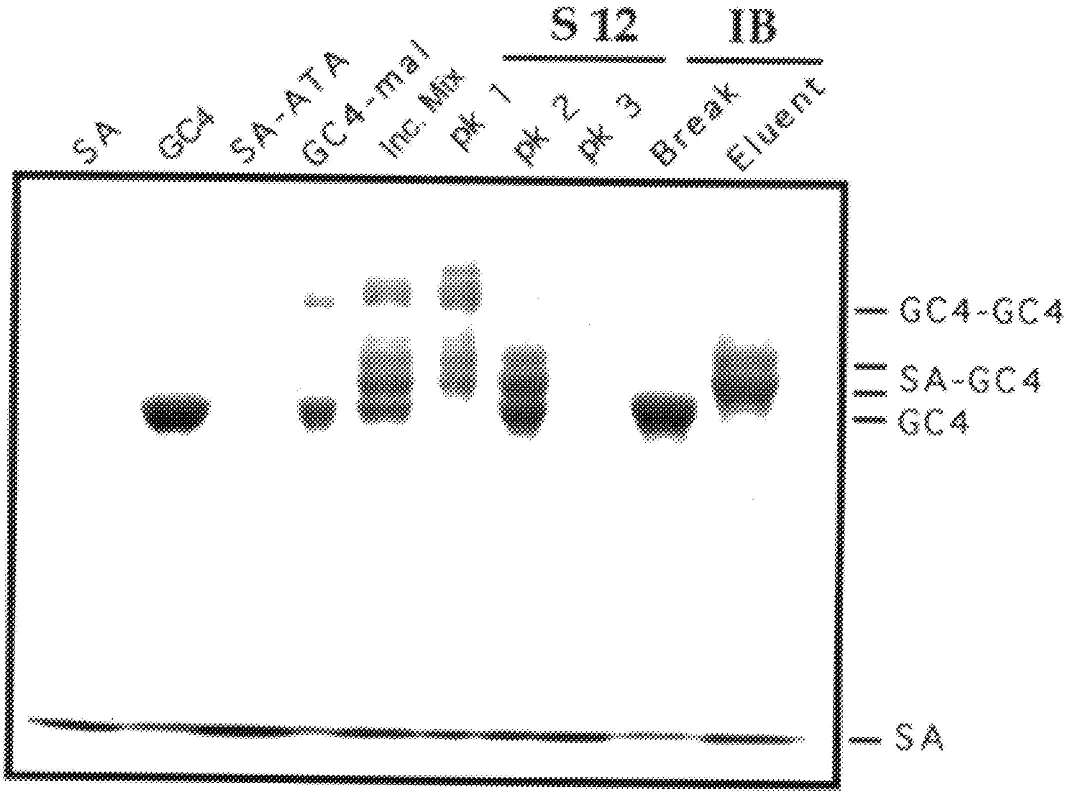
FIG. 12 represents SDS-PAGE analysis for the conjugation and purification of SA-GC4.

Equal molar, 0.65 μM, SA-ATA (Compound 5, Example IIB) and GC4-mal (Compound 8) were mixed in 0.05 $PO_4$/0.15M NaCl pH 7.5 buffer containing 1 mM EDTA and 0.05M $NH_2OH$ overnight at room temperature. The SA-GC4 conjugate was purified from unreacted GC4, SA and GC4-GC4 aggregates by size exclusion chromatography (SUPEROSE 12, Pharmacia, Piscataway, N.J.). For SUPEROSE 12 chromatography, the running buffer was 0.05 $PO_4$/0.15M NaCl pH 9.0 at 0.3 ml/min. For iminobiotin affinity chromatography, the second peak collected from the SUPEROSE 12 column was loaded with a 10 ml superloop onto a iminobiotin column. After the absorbance ($A_{280mn}$) returned to baseline, the GC4-SA conjugates were eluted by changing buffers to 0.1M sodium acetate pH 3.5. The eluent was then concentrated and the buffer exchanged by CENTRICON-30 centrifugation with 0.05 $PO_4$/0.15M NaCl pH 7.5 buffer. The eluted protein peak was analyzed by SDS-polyacrylamide electrophoresis (to determine the extent of crosslinking) using a Bio Rad mini-Protean II cell (Bio Rad Labs, Hercules, Calif.) and 8.5% polyacrylamide gels. The results are shown in FIG. 12. In the presence of SDS, SA dissociates into its 15 kdal subunits. Therefore, GC4-SA conjugates are evident as 15 kdal band increments heavier than 150 kdal GC4.

EXAMPLE VII

This example provides the method to investigate the coupling of the primary amines of SA with N-hydroxysuccinimide.

Figure 13A:
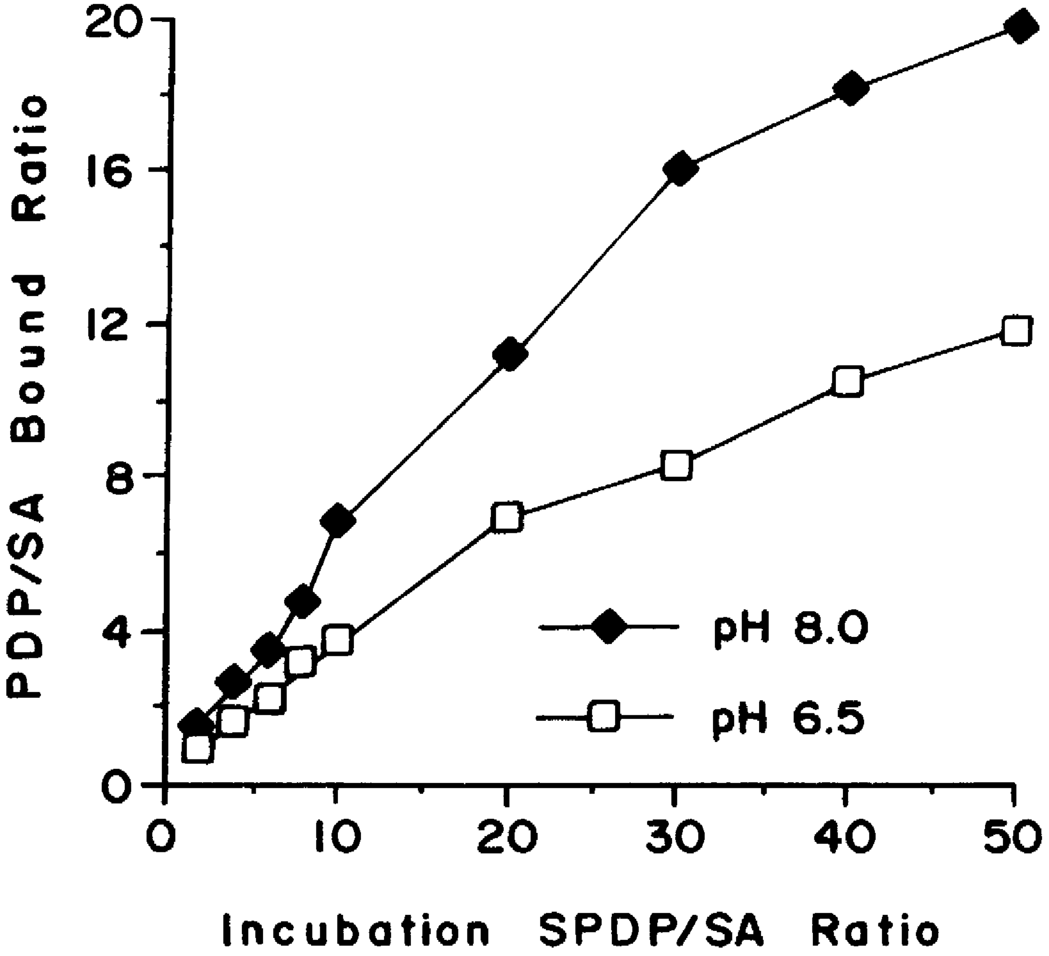
FIG. 13A is a graph representing the bound ratio of PDP/SA compared to the N-succinimidyl-3-[2-pyridyldithio]propionate (SPDP/SA) incubation ratio at pH 6.5 and 8.0.

N-Succinimidyl-3-[2-pyridyldithio]propionate (SPDP) (Pierce, Rockford, Ill.) solubilized in methanol was added to 5 mg/ml SA (International Enzymes, Fallbrook, Calif.) solution in molar SPDP/SA ratios ranging from 2–50 in 0.05 $PO_4$/0.15M NaCl pH 6.5 and pH 8.0. After a two hour incubation, free SPDP was removed from the bound adduct (PDP) by four washings on CENTRICON-30 filters (Amicon, Beverly, Mass.). For each sample, bound PDP was quantified spectrophotometrically by the release of pyridine-2-thione in the presence of 1 mM DTT ($E_{1,343nm}{}^{1M}$=8.08×$10^3$M). SA concentrations were also determined spectrophotometrically (E=34) by the release of release of pyridine-2-thione after disulfide bound cleavage with DTT. FIG. 13A graphs the bound ratio of PDP/SA compared to the SPDP/SA incubation ratio at pH 6.5 and 8.0. The maximum bound ratio approached 20, which is consistent with the total number of amines per mole of SA (16 lysine amino acids and 4 terminal amines).

Figure 13B:
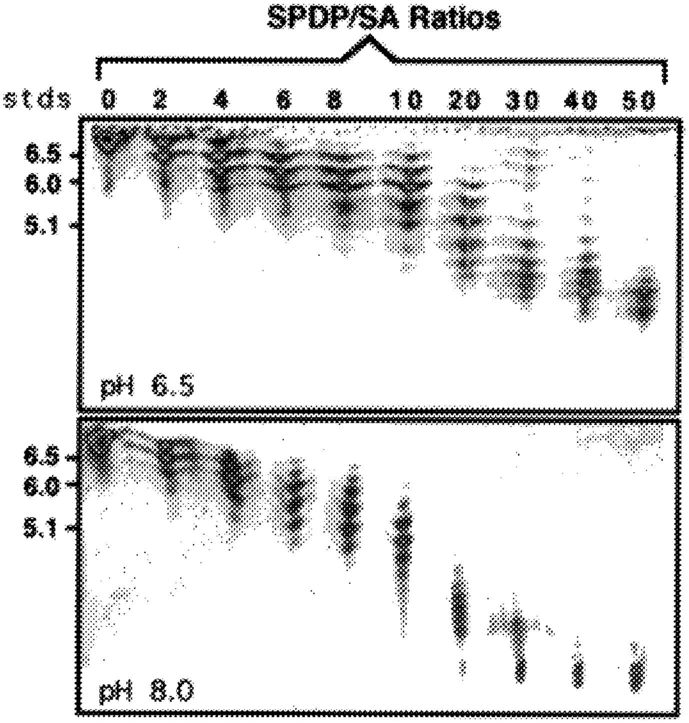
FIG. 13B represents isoelectric focusing analysis on SPDP/SA samples with different incubation ratios at pH 6.5 and 8.0.

Isoelectric focusing analysis on these samples, FIG. 13B, showed a decrease in pI associated with the degree of neutralization of the SA amines during PDP crosslinking.

SA was incubated with SATA (Compound 5, Example III) at a 6/1 SATA/SA molar ratio at pH 6.5 which gave an average PDP/SA ratio of 2. To confirm the extent of ATA crosslinking, hydroxylamine was added to ATA-SA, and the concentration of SH determined with Ellman's reagent. The resultant SH/SA ratio was 2.2.

Bound gal/SA-ATA (Compound 10, Example VII) and Tgal/SA-ATA (Compound 11, Example VI) ratios were 18 and 13 respectively as assayed by an anthrone calorimetric assay as reported by Roe [(1955) *J.Biol. Chem.* 212, 335–343]. For SA-Tgal, this is equivalent to an absolute galactose/SA ratio of 39.

The four terminal α-amines of SA are more reactive than the ε-amines due to their lower pKa and are thus preferred for cross-linking. The terminal amines are appropriate for cross-linking to monoclonal antibodies since the N-terminal domains are flexible and not involved in biotin binding or subunit association. Pahler et al (1987) *J. Biol. Chem.* 261:13911; Hendrickson et al (1989) *Proc. Natl. Acad. Sci.* 86:2190.

EXAMPLE VIII

Radiolabeling, Biodistribution and Imaging GC4-SA, (Compound 14, Example VI), gal-SA-GC4, (Compound 12, Example VI) and Tgal-SA-GC4, (Compound 13, Example VI) were radiolabeled with $^{131}$I or $^{125}$I by the Pierce Iodo-bead method (Pierce, Rockford, Ill.) and free iodine removed by ultrafiltration using CENTRICON-30 filters.

Figure 14A:
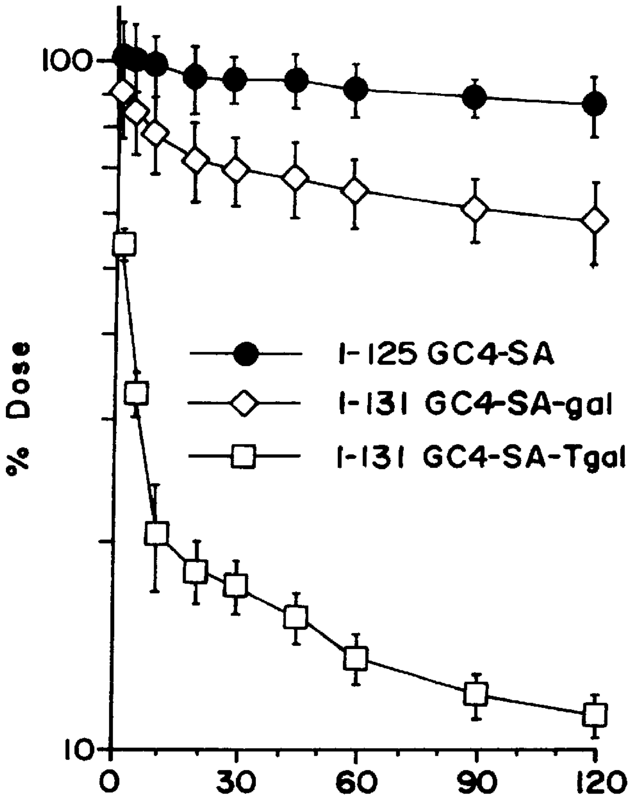
FIG. 14A is a graph representing a comparison of the blood clearance rates of $^{125}$-SA-GC4, $^{131}$I-gal-SA-GC4 and $^{131}$I-SA-Tgal-GC4.

Biodistribution was determined in vivo. New Zealand White rabbits, ~3 kg, were fasted for 12 hours prior to experiment and anesthetized using an intramuscular injection of chlorpromazine (25 mg/kg) followed by intravenous sodium pentobarbital (15 mg/kg). An external jugular vein was dissected and catheterized using a 5 French straight catheter for injection and collection of whole blood. The animal was placed in a supine position under the gamma camera for imaging and was then injected with ~75 μg (~30 μCi) of the radiolabeled proteins prepared above. Whole blood samples (2–3ml) were taken at intervals for 2 hours. Planar gamma camera images (30K count acquisition) were taken at 5, 30, 60 and 120 minutes. At two hours, animals were euthanized. Major organs were removed, weighed and representative samples taken for biodistribution analysis. Blood volume was estimated to be 6% of total body weight. FIG. 14A graphs the blood clearance of $^{125}$I-SA-GC4, $^{131}$I-gal-SA-GC4 and $^{131}$I-Tgal-SA-GC4. $^{125}$I-SA-GC4 had the slowest blood clearance, with approximately 87% circulating at 120 minutes. $^{131}$gal-SA-GC4 had faster clearance with ~59% circulating at 120 minutes and $^{131}$Tgal-SA-GC4 had the fastest clearance with ~21 and 11% circulating at 10 and 120 minutes, respectively.

Figure 14B:
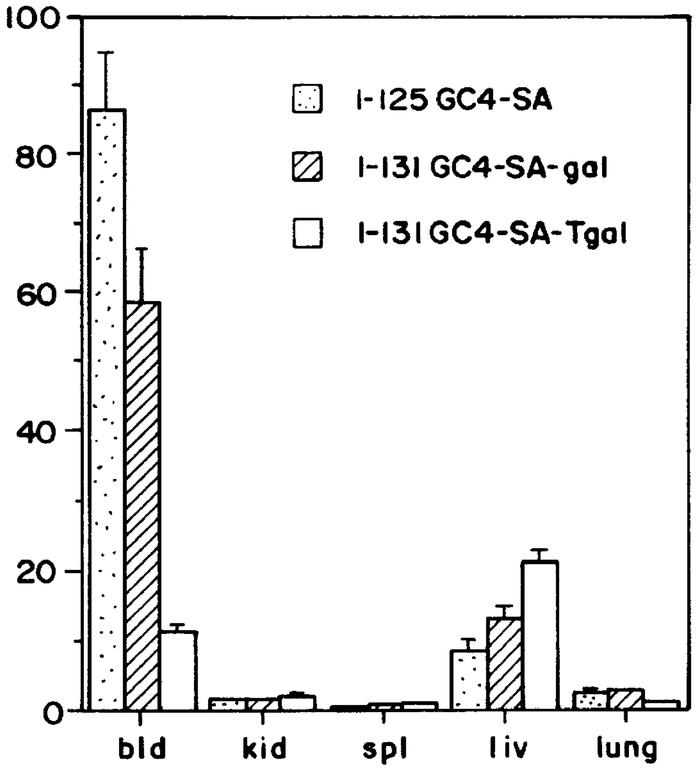
FIG. 14B represents the biodistribution of $^{125}$I-SA-GC4, $^{131}$I-gal-SA-GC4 and $^{131}$-SA-Tgal-GC4.

Biodistribution results, FIG. 14B, show a moderate increase in liver accumulation of $^{131}$I-gal-SA-GC4 and $^{131}$I-Tgal-SA-GC4 and minimal accumulation in other organs.

Figure 15:
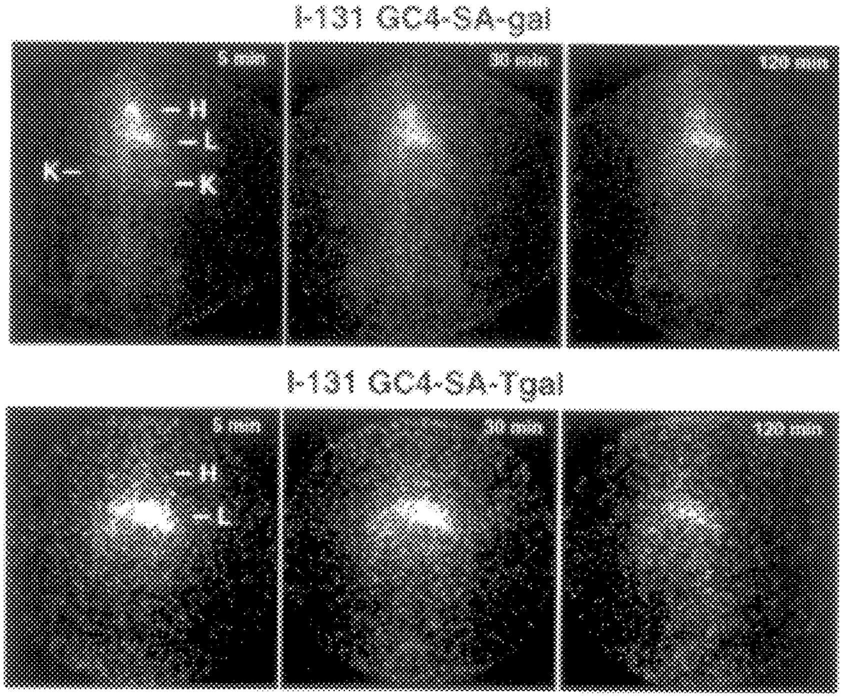
FIG. 15 is a composite of the nuclear images of $^{131}$I-gal-SA-GC4 and $^{131}$I-Tgal-SA-GC4 at 5, 30 and 120 minutes.

FIG. 15 is a composite of the nuclear images of $^{131}$I-gal-SA-GC4 and $^{131}$I-Tgal-SA-GC4 at 5, 30 and 120 minutes after injection into the rabbit. $^{131}$I-gal-SA-GC4 images are consistent with the pharmacokinetic results, as shown by heart, lung and blood activity, compared to the faster blood clearance and immediate liver accumulation of $^{131}$I-Tgal-SA-GC4.

I claim:

1. A conjugate of a targeting agent and a covalently modified streptavidin, wherein said covalently modified streptavidin contains at least one carbohydrate moiety, said carbohydrate moiety being galactose, mannose, fructose or lactose which is covalently attached to the streptavidin.

2. The conjugate of claim 1 wherein said targeting agent is a monoclonal antibody.

3. The conjugate of claim 2 wherein said monoclonal antibody is an anti-fibrin monoclonal antibody.

4. A conjugate of a trigalactose modified streptavidin and a monoclonal antibody, said trigalactose-modified streptavidin (SA) having the formula

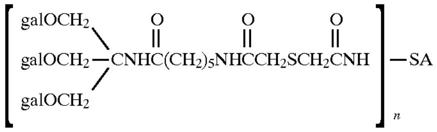

wherein n is 1 to 20 and gal is galactosyl.

5. A pharmaceutical composition comprising the conjugate of claim 1 or 4 and a pharmaceutically acceptable carrier.

6. A method of delivering a diagnostic agent to a target site comprising administering the conjugate of claim 1 or 4 to a host in an amount sufficient to bind to a target site; administering a detectable biotinylated compound under conditions sufficient to form a complex with target bound conjugate and at a dose sufficient for detection; and detecting said complex.

7. A method of delivering a therapeutic agent to a target site comprising administering the conjugate of any one of claim 1 or 4 to a host in an amount sufficient to bind a target site; and administering a therapeutically effective amount of a biotinylated compound under conditions sufficient to form a complex with target bound conjugate.

8. A compartmentalized kit for delivery of a diagnostic or therapeutic agent wherein said kit comprises a first container adapted to contain the conjugate of any one of claim 1 or 4.

9. The kit of claim 8 further comprising a second container adapted to contain a biotinylated compound.

10. The conjugate of claim 1 wherein said carbohydrate moiety is a galactose moiety.

11. The conjugate of claim 10 wherein said galactose moiety is covalently bonded to streptavidin through an amino group of streptavidin.

12. The conjugate of claim 10 wherein said galactose moiety is trigalactose.

13. The conjugate of claim 11 containing about 1 to about 20 galactose moieties.

14. The conjugate of claim 12 containing about 1 to about 20 trigalactose moieties.

15. The conjugate of claim 1 wherein the covalently modified streptavidin is trigalactose modified steptatvidin of the formula

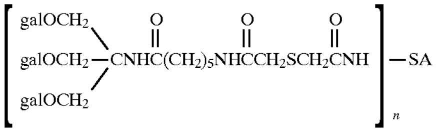

wherein n is 1 to 20 and gal is

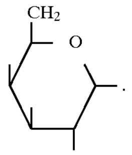

* * * * *

UNITED STATES PATENT AND TRADEMARK OFFICE

CERTIFICATE OF CORRECTION

PATENT NO. : 5,846,537
DATED : December 8, 1998
INVENTOR(S) : Scott F. Rosebrough It is certified that error appears in the above-identified patent and that said Letters Patent is hereby corrected as shown below:

Column 3,
Lines 58-59, "$^{131}$ I-gal-SA" should read -- $^{131}$ I-Tgal-SA --

Column 4,
Line 8, "$^{131}$ -SA-Tgal-GC4" should read -- $^{131}$ I-SA-Tgal-GC4 --

Column 15,
Line 50, "SEPHEDEX" should read -- SEPHADEX ® --
Line 52, "SA-Tqal" should read -- SA-Tgal --

Column 17,
Line 35, "$^{3}$ I" should read -- $^{131}$ I --

Signed and Sealed this

Twentieth Day of November, 2001

*Attest:*

Nicholas P. Godici

NICHOLAS P. GODICI

*Attesting Officer* *Acting Director of the United States Patent and Trademark Office*